(12) United States Patent
Rothman et al.

(10) Patent No.: US 10,737,140 B2
(45) Date of Patent: Aug. 11, 2020

(54) MULTI-FUNCTIONAL WEIGHT RACK AND EXERCISE MONITORING SYSTEM FOR TRACKING EXERCISE MOVEMENTS

(71) Applicant: Catalyft Labs, Inc., Cambridge, MA (US)

(72) Inventors: Jacob Rothman, Boston, MA (US); Nathaniel Rodman, Boston, MA (US)

(73) Assignee: Catalyft Labs, Inc., Cambridge, MA (US)

( * ) Notice: Subject to any disclaimer, the term of this patent is extended or adjusted under 35 U.S.C. 154(b) by 172 days.

(21) Appl. No.: 15/694,105

(22) Filed: Sep. 1, 2017

(65) Prior Publication Data

US 2018/0064992 A1 Mar. 8, 2018

Related U.S. Application Data

(60) Provisional application No. 62/382,418, filed on Sep. 1, 2016.

(51) Int. Cl.
*A63B 24/00* (2006.01)
*A63B 21/00* (2006.01)
(Continued)

(52) U.S. Cl.
CPC .... *A63B 24/0062* (2013.01); *A63B 21/00181* (2013.01); *A63B 21/0783* (2015.10); *A63B 24/0087* (2013.01); *G06F 3/011* (2013.01); *G06F 3/0304* (2013.01); *G06F 19/3481* (2013.01); *G06K 9/00342* (2013.01); *G16H 20/30* (2018.01); *H04N 7/18* (2013.01); *H04N 7/188* (2013.01); *A63B 21/0724* (2013.01); *A63B 2023/0411* (2013.01); *A63B 2024/0068* (2013.01); *A63B 2024/0081* (2013.01); *A63B 2024/0093* (2013.01); *A63B 2071/068* (2013.01); *A63B 2071/0677* (2013.01); *A63B 2209/02* (2013.01); *A63B 2209/08* (2013.01);
(Continued)

(58) Field of Classification Search
CPC ........... A63B 21/0783; A63B 24/0062; A63B 24/0087; A63B 2024/0071; G08B 13/1963
See application file for complete search history.

(56) References Cited

U.S. PATENT DOCUMENTS 4,416,293 A * 11/1983 Anderson .............. A63B 22/02 348/77
6,710,713 B1   3/2004 Russo
(Continued)

FOREIGN PATENT DOCUMENTS

CN 101996311 A 3/2011
WO 2015139145 A1 9/2015

OTHER PUBLICATIONS

ISA, "International Search Report", PCT/US2017/049911, dated Nov. 21, 2017.

*Primary Examiner* — Robert J Hance
(74) *Attorney, Agent, or Firm* — Intrinsic Law Corp.

(57) ABSTRACT

Systems and methods for tracking user movement during physical fitness activities are presented. A camera tracks movements of objects of interest in a field of view thereof during an exercise routine to log, instruct and provide feedback data to assist the user in reaching fitness goals. The user can also share his data with friends or teammates, for example through social media or in a client-server environment.

21 Claims, 17 Drawing Sheets

(51) Int. Cl.
*A63B 21/078* (2006.01)
*H04N 7/18* (2006.01)
*G16H 20/30* (2018.01)
*G06F 3/01* (2006.01)
*G06F 3/03* (2006.01)
*G06F 19/00* (2018.01)
*G06K 9/00* (2006.01)
*A63B 71/06* (2006.01)
*A63B 21/072* (2006.01)
*A63B 23/04* (2006.01)
*A63F 9/00* (2006.01)
*A63F 9/24* (2006.01)
*G02B 27/01* (2006.01)

(52) U.S. Cl.
CPC ....... *A63B 2220/16* (2013.01); *A63B 2220/18* (2013.01); *A63B 2220/20* (2013.01); *A63B 2220/24* (2013.01); *A63B 2220/30* (2013.01); *A63B 2220/40* (2013.01); *A63B 2220/51* (2013.01); *A63B 2220/805* (2013.01); *A63B 2220/806* (2013.01); *A63B 2220/833* (2013.01); *A63B 2220/89* (2013.01); *A63B 2225/055* (2013.01); *A63B 2225/15* (2013.01); *A63B 2225/20* (2013.01); *A63B 2225/50* (2013.01); *A63F 2009/0041* (2013.01); *A63F 2009/2435* (2013.01); *G02B 2027/0138* (2013.01)

(56) References Cited

U.S. PATENT DOCUMENTS

| | | | |
|---|---|---|---|
| 8,287,434 B2 | 10/2012 | Zavadsky et al. | |
| 8,503,086 B2 | 8/2013 | French et al. | |
| 9,072,929 B1* | 7/2015 | Rush | G09B 19/003 |
| 9,154,739 B1 | 10/2015 | Nicolaou et al. | |
| 9,195,304 B2 | 11/2015 | Shimomura et al. | |
| 2004/0037552 A1* | 2/2004 | Kajino | G08B 13/19619 396/427 |
| 2005/0175335 A1 | 8/2005 | Kajino et al. | |
| 2006/0082657 A1 | 4/2006 | Meier | |
| 2006/0294564 A1* | 12/2006 | Guillorit | A61B 5/0002 725/108 |
| 2007/0076944 A1 | 4/2007 | Bryll et al. | |
| 2007/0085913 A1* | 4/2007 | Ketelaars | H04N 5/232 348/239 |
| 2007/0146484 A1* | 6/2007 | Horton | H04N 5/247 348/159 |
| 2008/0285805 A1 | 11/2008 | Luinge et al. | |
| 2009/0100338 A1* | 4/2009 | Saetti | A63F 13/00 715/716 |
| 2009/0220124 A1 | 9/2009 | Siegel | |
| 2009/0233769 A1* | 9/2009 | Pryor | B60K 35/00 482/8 |
| 2009/0290023 A1* | 11/2009 | Lefort | G08B 13/19608 348/151 |
| 2010/0190610 A1 | 7/2010 | Pryor et al. | |
| 2012/0183940 A1* | 7/2012 | Aragones | A63B 24/0062 434/247 |
| 2012/0277891 A1 | 11/2012 | Aragones et al. | |
| 2013/0066448 A1 | 3/2013 | Alonso | |
| 2013/0072353 A1* | 3/2013 | Alessandri | A63B 21/0628 482/8 |
| 2013/0123667 A1 | 5/2013 | Komatireddy et al. | |
| 2013/0190135 A1 | 7/2013 | Pryor | |
| 2013/0224708 A1 | 8/2013 | Martin | |
| 2013/0326376 A1* | 12/2013 | Stachniak | G06F 3/03547 715/762 |
| 2014/0147820 A1 | 5/2014 | Snow et al. | |
| 2014/0228985 A1 | 8/2014 | Elliott et al. | |
| 2014/0270375 A1 | 9/2014 | Canavan et al. | |
| 2014/0270387 A1 | 9/2014 | Hoof et al. | |
| 2015/0072326 A1* | 3/2015 | Mauri | A61B 5/0488 434/247 |
| 2015/0074532 A1* | 3/2015 | Lapidot | G06F 3/017 715/719 |
| 2015/0196805 A1* | 7/2015 | Koduri | A63B 24/0087 482/6 |
| 2015/0255005 A1 | 9/2015 | Yoda et al. | |
| 2016/0323504 A1* | 11/2016 | Ono | H04N 5/2259 |
| 2016/0328093 A1* | 11/2016 | Ishii | G06F 3/0488 |

\* cited by examiner

MULTI-FUNCTIONAL WEIGHT RACK AND EXERCISE MONITORING SYSTEM FOR TRACKING EXERCISE MOVEMENTS

RELATED APPLICATIONS

This application claims the benefit of and priority to U.S. Provisional Application No. 62/382,418, entitled Multi-Functional Weight Rack for Tracking Exercise Movements, filed on Sep. 1, 2016, which is hereby incorporated by reference.

TECHNICAL FIELD

The present disclosure relates to performance assistance and safety for physical fitness apparatus such as those used by weightlifters or persons engaged in fitness training, especially using mechanical workout machinery.

BACKGROUND

As the population is becoming more health conscious, the fitness tracking industry has grown. Gym-goers are looking to technology to give them greater insight into their body and how they can achieve their goals faster. However, most of this fitness tracking technology take the form of wearables, which are usually worn on the wrist. These wearables are capable of tracking steps, heart rate, and calories burned. However, these are not metrics that a person who lifts weights (a significant portion of the population) gains the most value from. There is no affordable, reliable, and easy-to-use use fitness tracking technology on the market that can provide weightlifters with the level of insight they desire.

Conventional weight racks are large, stationary items that hold weights when the weight lifter isn't exercising. When weightlifters are lifting free weights on one of these racks, it is recommended that they receive assistance and supervision from a person referred to as a "spotter." Spotters reduce risk of injury and promote enhanced performance gains by allowing weight lifters to push themselves to failure without risk of injury. However, properly trained spotters are often difficult to find, and spotters are often not capable of preventing certain, more serious weightlifting accidents from happening (e.g., a weightlifter dropping a weight on him/herself).

The present disclosure overcomes some or all the prior deficiencies, and provides an innovative useful system and method for assisting those exercising or training others using mechanical moving structures.

SUMMARY

As described, there are many reasons to exercise or carry out physical training with the assistance of exercise machines (mechanical, electro-mechanical, hydraulic, etc.). A user (whether an athlete, student, patient, or anyone interested in gaining or maintaining physical fitness) commonly adapts features of an exercise machine to suit his or her needs or goals. For example, a weight lifter will choose a weight setting or a resistance setting to exercise certain muscles, adjust various mechanical lever arms of a machine, and so on. Each of these adjustments results in a differing amount of quantitative or qualitative exercise, which users often want to track or monitor, e.g., to confirm that they are progressing in an exercise regimen. Also, a user's coach, physical therapist, parent, friend, team mate, or other person may be interested in monitoring or logging the activities of the user. Such scenarios are typically tedious to track and monitor because they lacked an automated way to do this tracking and monitoring. Typically, a user is a member of a club or gym and maintains an exercise card for him or herself, which is usually a hand-written piece of paper the user can write in to log the activity, date and nature thereof. Some simple software applications (apps) exist to track workouts as well, but they similarly require the user to open the app and manually enter the information into a device such as a smartphone running the app.

Aspects of this invention include an exercise monitoring system for use with exercise equipment, comprising a camera assembly having at least one imaging sensor configured and arranged to generate a grid of pixel data representing distance from a reference point to a point in space or object represented in said grid of pixels, or, a distance matrix image; a motorized driver that moves said camera assembly in at least one degree of freedom to track a movement of at least one object in a field of view of said at least one imaging sensor; a processor coupled to said camera assembly and receiving distance matrix imagery from said camera assembly; a controller, in data communication with said processor, and coupled to said motorized driver, which controls movement of said motorized driver so as to track the movement of said object; a housing containing each of said camera assembly, motorized driver, processor and controller, the housing further configured to mechanically couple said exercise monitoring system to an external support.

In an embodiment, an imaging sensor comprises a visible light image capture camera assembly. In another embodiment, the imaging sensor comprises a three-dimensional camera assembly. In yet another embodiment, the three-dimensional camera assembly comprises one distance imaging camera or a plurality of such cameras, which can include visible light or infra-red image sensors, spatially separated from one another and configured and arranged to capture respective infra-red imagery and further being coupled to a processor that computes a position for each pixel in a multi-pixel position image based on said infra-red imagery from each of the plurality of infra-red image sensors.

In some embodiments, the housing further comprises one or more mechanical attachment members that secure the system to a support member of said exercise equipment; or, the mechanical attachment members comprise a strap that secures the system to a support member of said exercise equipment.

In other embodiments, the system includes a motorized driver comprising a servo motor that applies reversible torque through a gear to rotate said camera assembly about an axis of rotation so as to adjust an angular position of said camera assembly with respect to said housing.

And in other embodiments, the system includes a communications module wherein said communications module is configured to send and receive data signals over a communications network, for example to allow communication between an exercise monitoring system, camera assembly, user interface, and/or a remote server or client machine, e.g., from which the user can receive instructions or feedback and to which the user's activity is transmitted.

Some embodiments may include a tilt angle sensor, e.g., an accelerometer, which permits sensing an angular position, displacement, acceleration or other movement of the camera assembly about at least one degree of freedom. In an embodiment, the degree of freedom is a rotational movement about an axis, e.g., to tilt the camera assembly upwards or downwards to track a moving object of interest such as a barbell or other piece of exercise equipment.

The system can include processors or processing circuits that execute machine-readable instructions. Processors can be co-located, on a same or distributed circuit board, and may for example be placed in the exercise monitoring system, the camera assembly, the interactive user device, or on a remote computer in the cloud or elsewhere. These processors can implement an exercise program. The processors can also carry out so-called artificial intelligence, machine learning or similar programs to develop an improved or more accurate capability to recognize objects of interest in a field of view of the cameras of the system.

In some aspects, the system's camera assembly includes a three-dimensional (3D) camera device that can determine a distance from a reference point to another point in the FOV of the camera (e.g., a point on the exercise machine or barbell in use). An image containing multiple pixels, each pixel representing a distance to the respective object imaged at that pixel can be generated by a processor in or coupled to the 3D camera. For example, using geometric relationships (trigonometry), a camera system with multiple (at least two) spatially separated apertures can use a parallax thereof to determine a distance to a point in the FOV. Also, the processor can then take a time sequence of such distance measurements in a matrix of distance measurements (e.g., pixels in a Cartesian FOV) and determine a rate of change in the position of an object, i.e., its velocity. Similarly, a rate of change of the velocity may be used to compute an acceleration. If the mass of a moving object is known (or entered by the user or a coach) the system can likewise perform any number of useful calculations to determine force, energy, calorie use, or other computations helpful to achieving or monitoring the user's activities on the machine.

In an aspect, the exercise monitoring and/or the interactive user device are moveable from one machine to another, or from one location on the machine to another. This allows flexibility in the system's use, and eliminates the need for every machine in a weight room to need its own camera and monitoring apparatus, saving cost.

Other aspects of the invention include a method for tracking an exercise routine of a user, comprising providing an exercise monitoring system in a housing mountable to an exercise machine; collecting imagery using at least one distance-measuring camera assembly in said exercise monitoring system, the imagery containing information regarding an object of interest in said exercise machine; generating a multi-pixel position image from said imagery that codifies, for each pixel in the multi-pixel position image, a distance from a reference point to a corresponding point on said object of interest; and moving said camera assembly of said exercise monitoring system as necessary to track a position of said object of interest and to keep said object of interest within a field of view of said camera apparatus.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

This disclosure is directed to a system that includes a 3D camera, a computer, a touchscreen display, and mounting hardware that can be mounted to weight racks to track a weightlifter's movements throughout a workout. With this technology, a weightlifter can automatically track his sets, number of repetitions (reps), barbell velocity, power output, and bar path. The technology can also track body position, and therefore an athlete will not be limited to workouts that require a barbell. As would be appreciated by those skilled in the art, and as can be understood from the disclosure below, the present disclosure can also be applied to other mechanically-assisted fitness training programs, including those that use weight bars, ropes, pulleys, gears, elastic tension members and other such moving parts that are part of a system for physical conditioning, exercise, therapy or weight lifting programs.

The technology can provide weightlifters greater insight into their workouts by providing them with information they couldn't obtain before and allowing them to more easily track their progress over time. The technology can also make weightlifting more accessible to people by tracking form and preventing injury. Embodiments of the technology also provide the weightlifter with automatic assistance (or a "spot"), which can improve the weightlifter's safety.

This invention is also useful for trainers, coaches, parents, physicians, athletes or other persons wishing to track the progress or analyze the exercise and development of an athlete, patient, team member or other subject. In an embodiment, the apparatus on which the subject is training (generally a weight rack or exercise machine) is adapted with optical and/or motion sensors as described herein.

Figure 1:
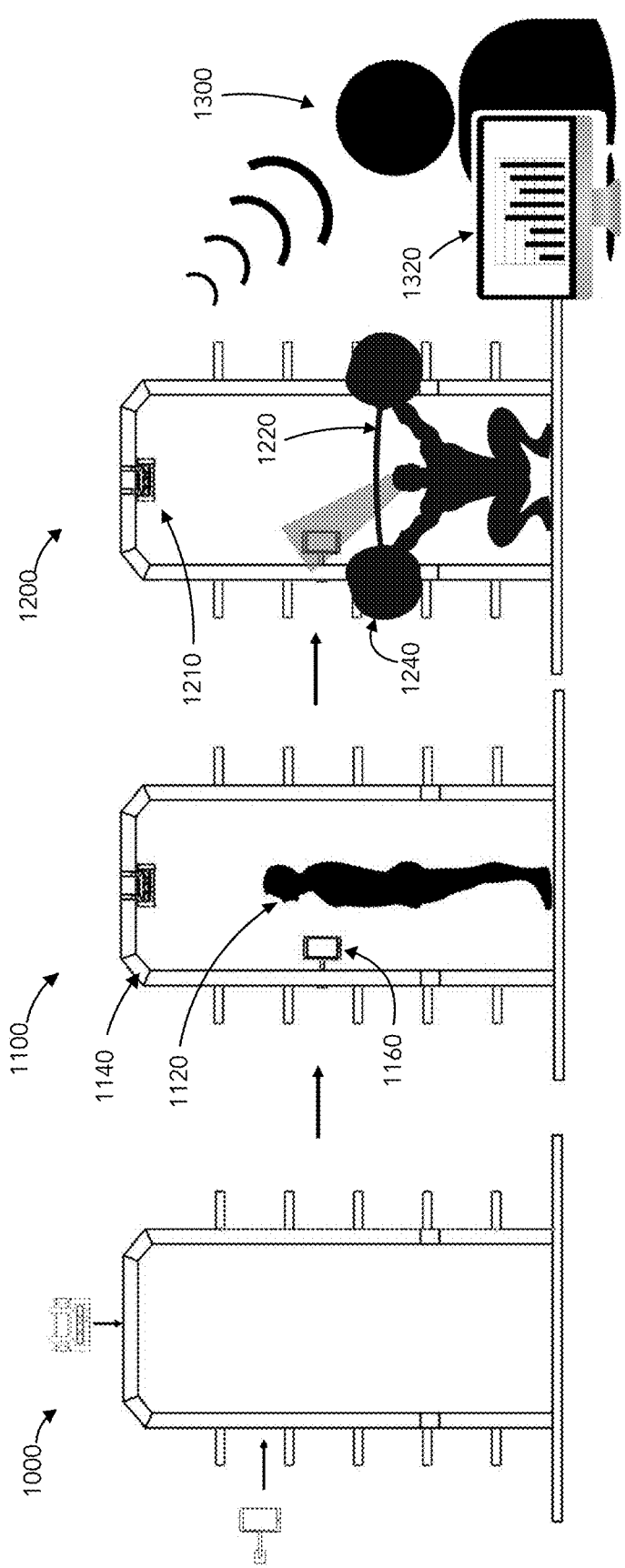
FIG. 1 illustrates a use instance of the present technology as relates to an example of a user lifting weights.

FIG. 1 shows a use instance of the present technology at 1000 including some components or architecture according to aspects referenced. In system 1100, the user 1120 (e.g., weightlifter) approaches the rack 1140. Rack 1140 may comprise a fixed weight rack having various rigid members and facilitating one or more exercises, supporting a weight lifting bar, barbell, resistance members or other mechanical exercise equipment (generally, 1220) in use by user 1120.

The user 1120 interacts with a user interface unit 1160 that may comprise a computer, tablet, mobile device, touch screen, or other interactive apparatus. The user can receive or see or hear information provided by the interactive device 1160 as well as provide or enter information into the device 1160. In an embodiment, the interactive device 1160 is a communications-enabled tablet such as a commercially available tablet device, with a visual display and touch screen user interface, and coupled to a communications port or network, by wired or wireless means. The interactive device 1160 may comprise a processing circuit, local memory, which together can hold and execute machine-readable instructions to carry out program functionality on device 1160, and which may further be equipped with an operating system such as Android® or Apple iOS® or another system.

The user 1120 can be one of several users allowed access to an interactive device 1160, or may bring his or her (e.g., his) own personal device 1160 for such purpose. The user 1120 logs in, for example by entering his name or a user ID code. Once access is granted to the software on device 1160, user 1120 can select or enter a chosen activity or exercise type (e.g., squat, half squat, etc.), and weight 1240 that he will be using on a keypad or touch screen display of interactive device 1160 or similar input interface. In some aspects, the user 1120 can also choose what metrics he wants displayed during the workout (e.g., bar velocity, power output, bar path, number of reps, etc.). In other aspects, user 1120 may interact with a trainer, physical therapist, doctor, coach, team mate, or friend (e.g., coach) 1300, who may be located remotely from the site of the exercise system at 1100 but connected thereto over a communications network as will be discussed in more detail below.

At least some of this information can be entered remotely (e.g., using a computer program and interface, an application or "app" on a smartphone or tablet 1320, or through a website available to a remote client) by another user, monitor, physician, coach 1300, etc.

After the user 1120 logs in and information is entered on interactive device 1160, the user begins his workout at 1200. During the workout, a exercise monitoring assembly 1210 tracks the barbell 1220 in space. In an aspect, the exercise monitoring assembly 1210 may comprise one or more camera assemblies and/or optical components to capture an image of an environment of weight lifting equipment (e.g., barbell 1220) or other relevant objects in the field of view of the one or more camera assemblies of exercise monitoring assembly 1210.

By tracking the barbell 1220, a computer receiving images from exercise monitoring assembly 1210 can determine a two- or three-dimensional (3D) position of the barbell 122. This information can be used to measure a displacement, velocity, and/or acceleration of the barbell as a function of time, or other relevant data concerning the user's workout. The number of repetitions (reps) that the user has made and the path of the bar and/or the user's body position can be used to determine the user's form in performing the exercise and other useful information.

The display of interactive device 1160 can display the chosen metric(s) on the user interface for each rep or for each set or exercise session as a whole. When the user racks (replaces) the weight after the set, the system can automatically record a finished set.

System 1000 is preferably in communication with a computer, server or cloud network that stores the user's data, for example in a database coupled to the computer, server or cloud network as will be discussed further below. The user 1120 and/or his coach 1300 can then access the information remotely, e.g., using an executable program, machine-readable instructions set, software application or "app" on a smartphone or tablet, or through a website, to review the user's exercises and to compare one day's exercise data with another day's exercise data. The user or coach can review all the relevant metrics including watching and annotating RGB video of their past workouts. The user can also access some or all of this information using touch screen of interactive device 1160.

Optionally, the system can keep logs of the activity, goals and progress of a user. For example, in an aspect, the system may generate video records or photographic snapshots of key images of interest, as well as update a data log, during the course of an exercise session. Optionally, these images or video segments can be viewed on demand and can be stored for a short or long time on a media storage device, e.g., a data store, either locally or remotely.

There may be cases when specific users or organizations have different needs and may require a slightly different process. In the case of a strength and conditioning coach/trainer working with varsity athletes, professional athletes, high school athletes or clients, the coach may have the option to upload a user's workout beforehand so that when an athlete logs in, the sets, reps, weight, and power output/velocity goals are already listed on the display of interactive device 1160.

Thus, the technology can be used to track the user's performance and to compare the user's performance with a pre-set goal. The pre-set goal can be entered by the user or by a third party, such as the user's coach or trainer. The system can notify the third party (or another third party) if the user does not reach the pre-set goal. Alternatively, the system can propose a goal for the current workout based on the user's past performance or based on a long term goal.

In some embodiments, the user 1120 can select or invite friends or team mates to join a group of users, for example to train together or to motivate each other. The invitation of friends can occur by entering each friend's user name, email address, phone number, or other unique identifier. In some embodiments, the user can connect his profile over social media to share his exercise results or goals, or to invite friends to a join a group of users, as discussed above.

Additional features of the technology, according to some aspects, can include the ability for coaches/trainers to upload workouts beforehand; facial recognition to recognize athletes to identify them or access their profiles automatically; using camera vision (above-described 3D depth camera or additional CMOS cameras) to recognize weight; load cells to recognize weigh; machine learning and camera vision to recognize the exercise being performed.

The present paragraphs describe preferred, but only exemplary examples of the hardware components of the technology according to one or more embodiments. It is noted that some embodiments can include additional or fewer hardware components than the examples described below. For example, a component may be lumped or distributed in various implementations (i.e., located on one circuit board, in one housing, at one location, or may be alternatively divided into multiple co-located and/or remote parts). An implementation would depend on the needs and specific components used in a given instance and are flexibly available as known by those skilled in the art.

As described, a camera, optical or imaging apparatus (generally "camera"), which may include one or more such devices operating in unison, is used to determine a position of one or more objects of interest such as an exercise machine part. In an aspect, a 3D depth camera is used to get the coordinates of a barbell in 3D space. The camera 1210 returns a depth or distance image, which can be stored as an electronic file representation. The known position, e.g., height and orientation of the camera may be used to take the information from the depth image and place the bar in the world coordinate system. In another example, a CMOS camera may be used for this purpose.

Figure 2:
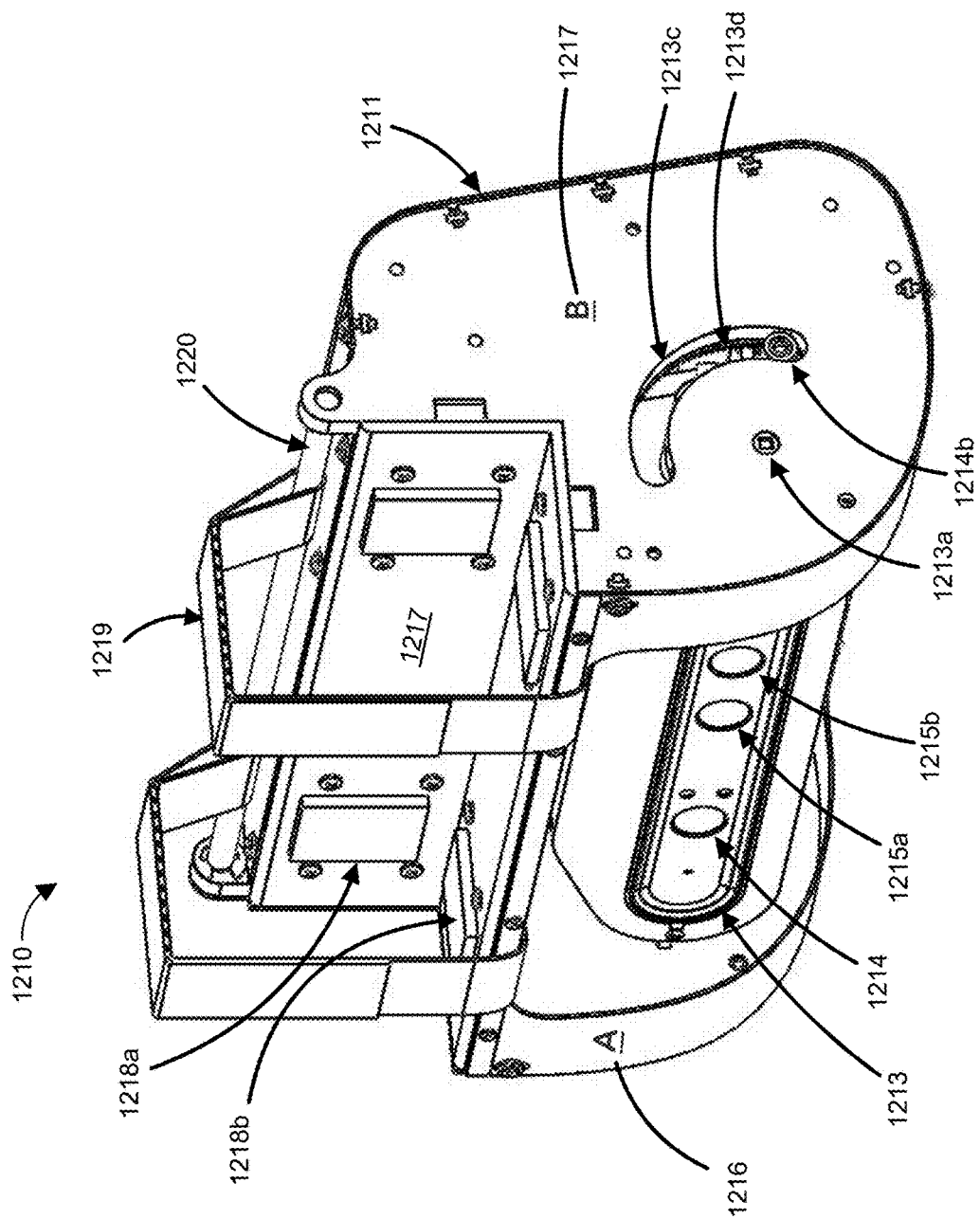
FIG. 2 illustrates a perspective view of an exemplary exercise monitoring system and camera assembly and housing according to an example hereof.

FIG. 2 illustrates a perspective view of an exemplary exercise monitoring assembly 1210 as described herein. The exercise monitoring assembly 1210 comprises a housing 1211, which may be made from a solid molded polymer material (e.g., plastic), and which further comprises structural, imaging, sensing, attachment, communications and other components. Housing 1211 generally has several faces including a front face A, 1216, that faces towards the user and the exercise equipment of interest during use so as to capture the needed field of view (FOV). Exercise monitoring assembly housing 1211 also has other facets such as side face B, 1217.

As mentioned previously, the exercise monitoring assembly 1210 would include one or more optical sensors, e.g., camera system 1213. In the shown non-limiting example, a red-green-blue (RGB) sensor (camera) 1214 is provided and can generate conventional imagery (still or video) of a scene in the FOV of the camera system 1213. In addition, one or more infra-red cameras 1215a, 1215b substantially share RGB camera 1214's FOV and are disposed in a same face of the exercise monitoring assembly housing 1211, in this example in or along front face A, 1216.

Some 3D cameras do not have a large enough field of view to cover all possible exercises that an athlete could perform around the rack. In an aspect, the invention can incorporate motorized drive, e.g., a servo motor, DC motor, AC motor, or other prime mover, into the system to allow for precise positioning of the camera, allowing us to see all exercises regardless of where they are being performed. The accelerometer can be used to provide closed loop feedback for the servo as well as to provide the camera vision with a precise location. The servo and accelerometer may be controlled by a small microcontroller. In addition, or in the alternative, a camera with a wider field of view can be used.

In various embodiments, camera system 1213 is designed to translate and/or rotate with respect to housing 1211 so as to track or follow the movement of objects in its FOV. In the illustrated example, camera system 1213 as a whole can pivot (rotate) about an axis 1213a within its housing. To do so in this exemplary embodiment, a motor is operated to traverse a bearing, bushing, gear or pinion 1213b along a crescent shaped slot 1213c in said housing, following the curve of a toothed track 1213d. Those skilled in the art will understand that these exemplary embodiments are not limiting, and that other ways can suitably be used to rotate the camera(s) up and down, for example to follow a moving barbell or other exercise tool as it is raised and lowered by a user.

An accelerometer mounted to the camera system 1213 may be used to determine the precise angle of the camera 1213. By adding an accelerometer to the system, it may not be necessary to use precision mounting components, allowing for easier mounting to a wider variety of weight racks. As stated before, given the flexibility of the mechanical mounting of the present system, this system can be adapted for use in a wide variety of exercise equipment, including various cross-sections of brackets, bars, supporting structures thereof, and including in mounting on or to fixed items in the environment of the exercise equipment and dedicated tripods, etc.

Figure 17:
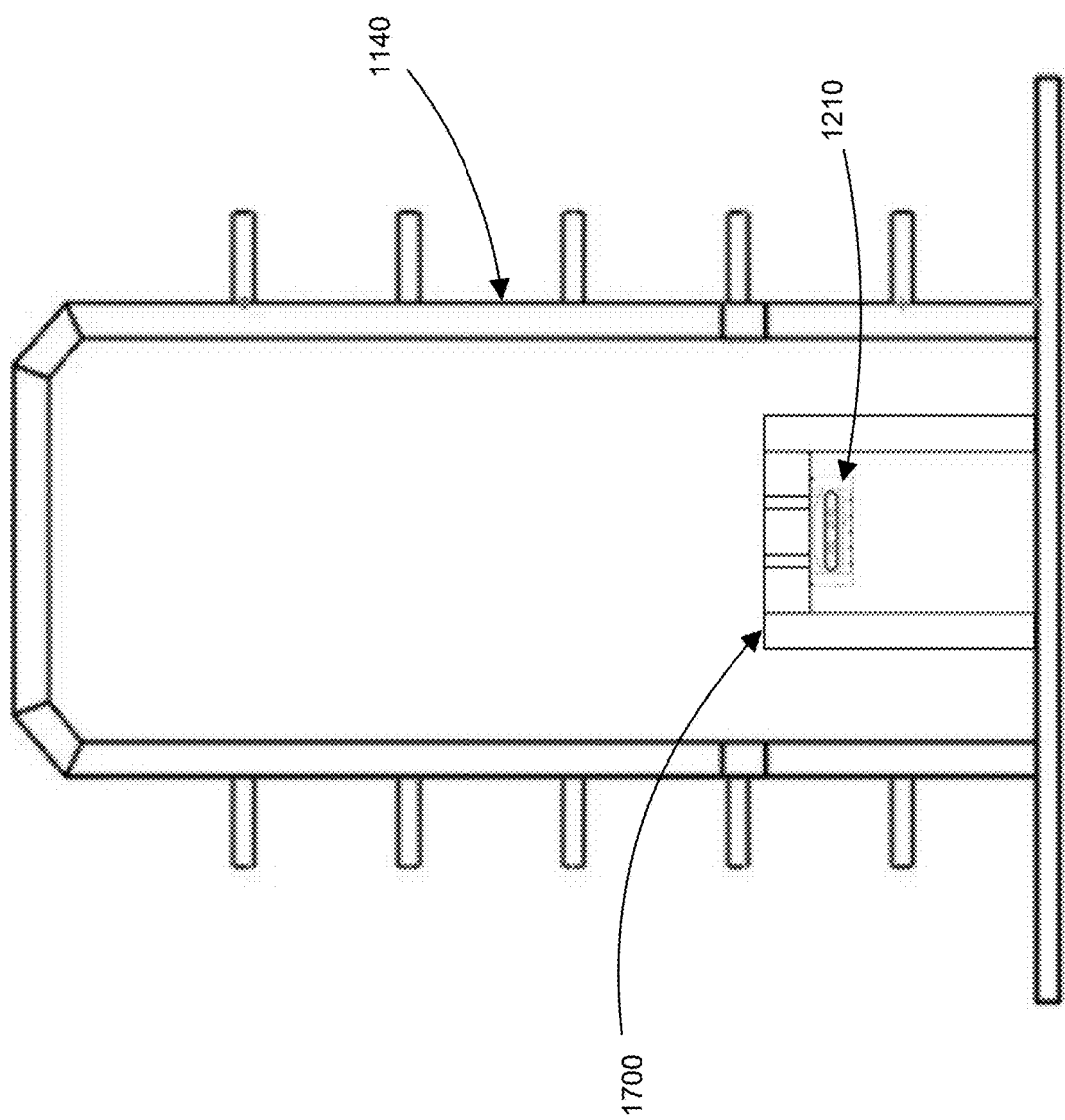
FIG. 17 illustrates an exemplary camera mounting platform for use herewith.

A stand-alone, yet portable, support mount may be provided (see, e.g., FIG. 17) to which the camera assembly and other components of this system can be affixed. Once in place, the support mount is made to face the exercise equipment and/or user so that the distance-measuring imagers can generate a matrix of pixels (e.g., an image of rows and columns) representing respective distances from a reference point (e.g., on the camera assembly)

In one aspect, the camera mount comprises an exercise monitoring assembly mounting structure, which may be in the form of an aluminum L-shaped extrusion or bracket 1217. But the material is not limited to aluminum. Molded plastic or other solid materials can similarly be used to construct the exercise monitoring assembly mount. In an embodiment, a L-shaped bracket (which is fixed by glue, rivets, bolts or other means to housing 1211, and in some cases forms part of housing 1211) contacts the exercise equipment rack on one or more (e.g., two) internal faces of the rack. Rubber pads 1218a, 1218b may be disposed between the L-extrusion 1217 and the weight rack to prevent damage to the rack and to increase frictional hold.

In addition, webbing or straps 1219 may be used to hold the L-extrusion 1217 and housing and assembly 1210 firmly to the exercise rack, whereby the straps are wrapped around a solid (e.g., metal) bar 1220 fixed across housing 1211 to allow sufficient tensioning of straps 1219. In an example, one or more hook-and-loop straps 1219 are used to secure the exercise monitoring assembly 1210 to a suitable and stable member of the exercise machine apparatus. But elastic bands, leather belts or any other mechanical fixation implements can be used to temporarily or permanently mount the cameras thereto. While the securement means shown in the illustrated example are adapted for fixing the apparatus to a square cross-section, other configurations are possible, e.g., for round cross-sections. Again, the mechanical securement means described here is not intended to limit the invention, and those skilled in the art can appreciate alternative ways to achieve the same or similar ends by equivalent means.

Figure 3:
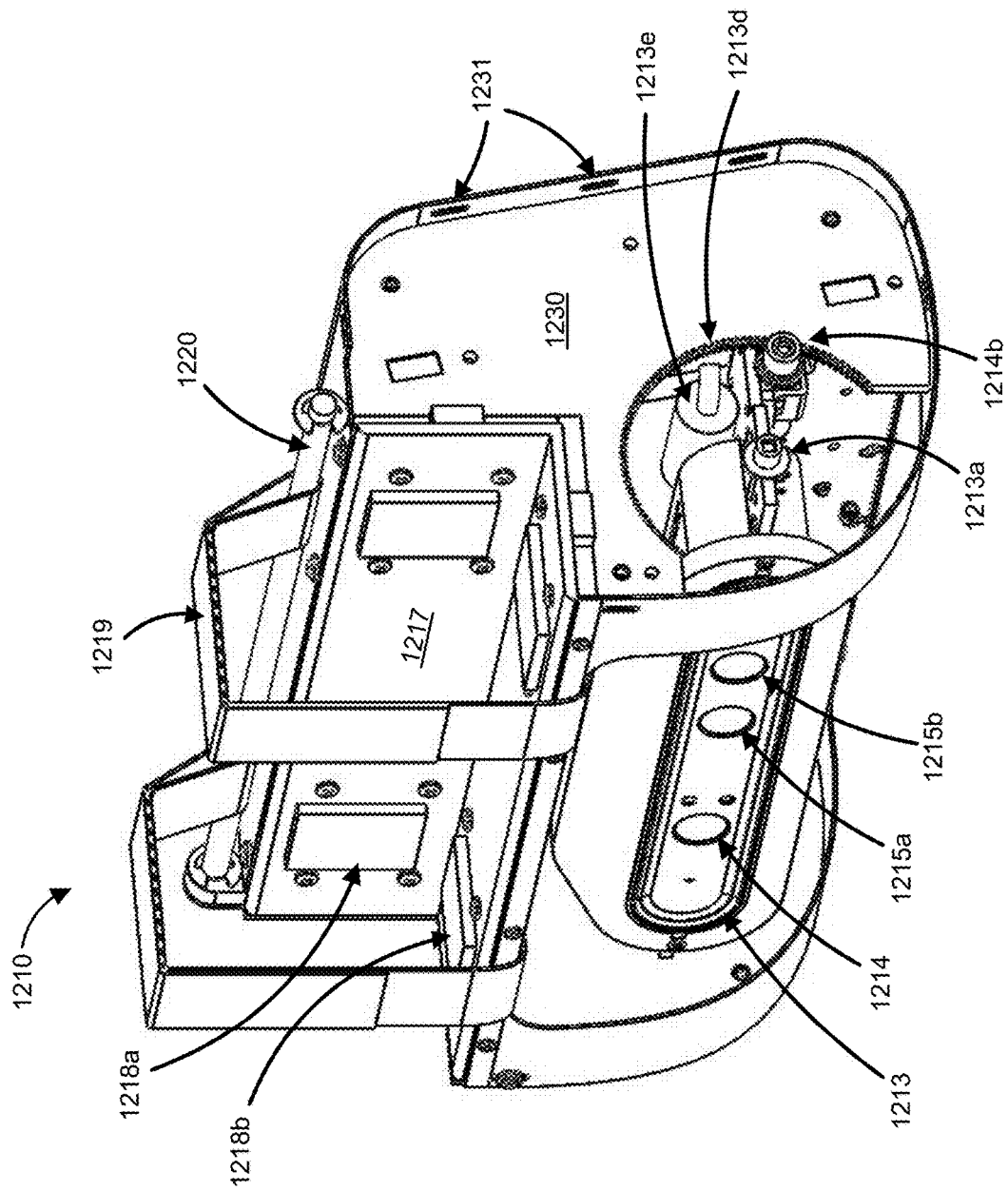
FIG. 3 illustrates a perspective view of an exemplary exercise monitoring system and camera assembly with the housing thereof removed to show some internal components of the system.

FIG. 3 illustrates a view of the exercise monitoring assembly 1210 without its shroud or housing 1211 to better visualize certain internal parts. A metallic or solid frame 1230 is used to attach, support and protect the internal components such as the camera system 1213, the rotation servo motor and gears assembly described earlier, and to firmly attach a plastic housing 1211 to the frame 1230, e.g., at snap or screw connection locations 1231. Frame 1230 may be a stamped, cast, machined or laser-cut metal, carbon fiber, hard plastic or other article of manufacture.

It can also be appreciated that the ability to move the present exercise monitoring assembly 1210 from one location to another or from one machine to another allows flexibility of use and can reduce the need/cost for additional units because the moveable assembly can be transported as desired from one exercise station to another. Other embodiments may include magnets, suction cups, or other form of clamping mechanisms. In some examples, the exercise monitoring assembly 1210 can be placed securely on a portable stand such as a tripod or other mechanical coupling that allows the exercise monitoring assembly to be secured with respect to the exercise equipment yet maintain the needed field of view. These implementations are available to those skilled in the art and users of the present invention according to their specific needs and are not limiting of the present implementation.

A computer, processor or computing device is used to run the application by executing machine-readable instructions and performing the needed image processing. In a non-limiting example, a circuit, integrated semiconductor device, application specific integrated circuit (ASIC), circuit board, or combined hardware-software processing assembly (generally, processor) can include some commercially-available image processing-capable hardware such as the TK1 or TX1 products from NVIDIA®. But of course, those skilled in the art, today or in the future, would appreciate that general purpose processors (e.g., from Intel, Texas Instruments, Samsung or otherwise) as well as specialized graphics processors can be adapted for the present use as well. The processor can connect to a data communication network such as the internet or any network and store data/videos, etc. on a connected server. The computer may be a small, stand-alone computer. However, it may also comprise a tablet or other device, which will serve as our computer and touch screen display.

Figure 4:
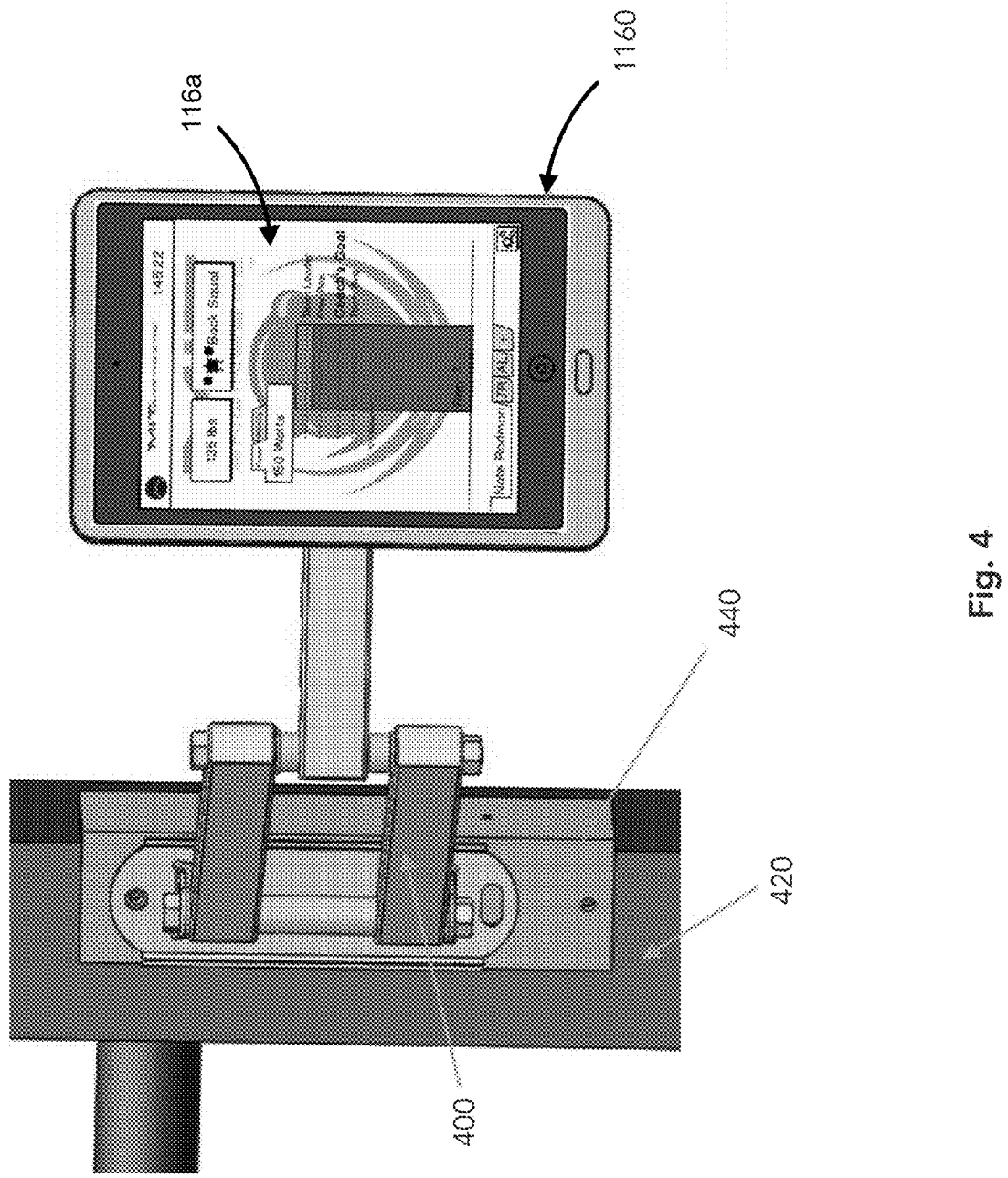
FIG. 4 illustrates an interactive device or user interface mounted on a swiveling mounting armature.

FIG. 4 illustrates an example of an interactive use input/output (I/O) device 1160 as described earlier, mounted to a mechanical swivel mount 400 that can be integrated with or coupled using a bracket 440 to a support member of an exercise machine 420, or alternatively, to a stand-alone support such as a tripod. In some embodiments, a display mount, similar in form to the camera mount described above, may be used. In one example, there can be an additional component similar to a standard TV wall mount. This gives the display the flexibility to position at any angle or position—as is most convenient for the user. The display mount may be removed to allow easy repositioning and installation. The interactive device 1160 includes a display screen 116a, for example, a touch type display interface, that can serve as a point of contact the user has with the system while exercising. The display 116a can present a graphical user interface (GUI) in some aspects, showing immediate feedback on barbell velocity, power output, and bar path. It can also allow a user to input (or select) his name, ID number, exercise plan and more via a touch screen or similar input function. The system can accept entries according to the programming of the application, including entries relating to the user's height, weight, age, the amount of weight being lifted for a given exercise, and other information. In other embodiments, e.g., consumer versions, the system may be used without a specialized display, but instead, may utilize a user's existing smartphone or tablet running an appropriate application to display the data and act as an I/O terminal for the present purposes.

In another aspect, the present system can optionally combine the computer and display modules into a tablet, and providing a front facing camera on the tablet can allow for user facial recognition. This can be used as a source to gather RGB video from another angle, allowing coaches and athletes to more easily review footage of their lifts. Said front facing camera may be attached to the display in one or more embodiments.

As mentioned elsewhere, the present exercise monitoring assembly 1210 can be provided in a exercise monitoring assembly including one or more camera assemblies. A camera system includes one or more camera assemblies, each generally having an optical sensor coupled to a processor, and that may be an optical camera (still or video type) and may be sensitive to wavelengths of electromagnetic energy in the visible range or in another range such as the infrared range.

Figure 5:
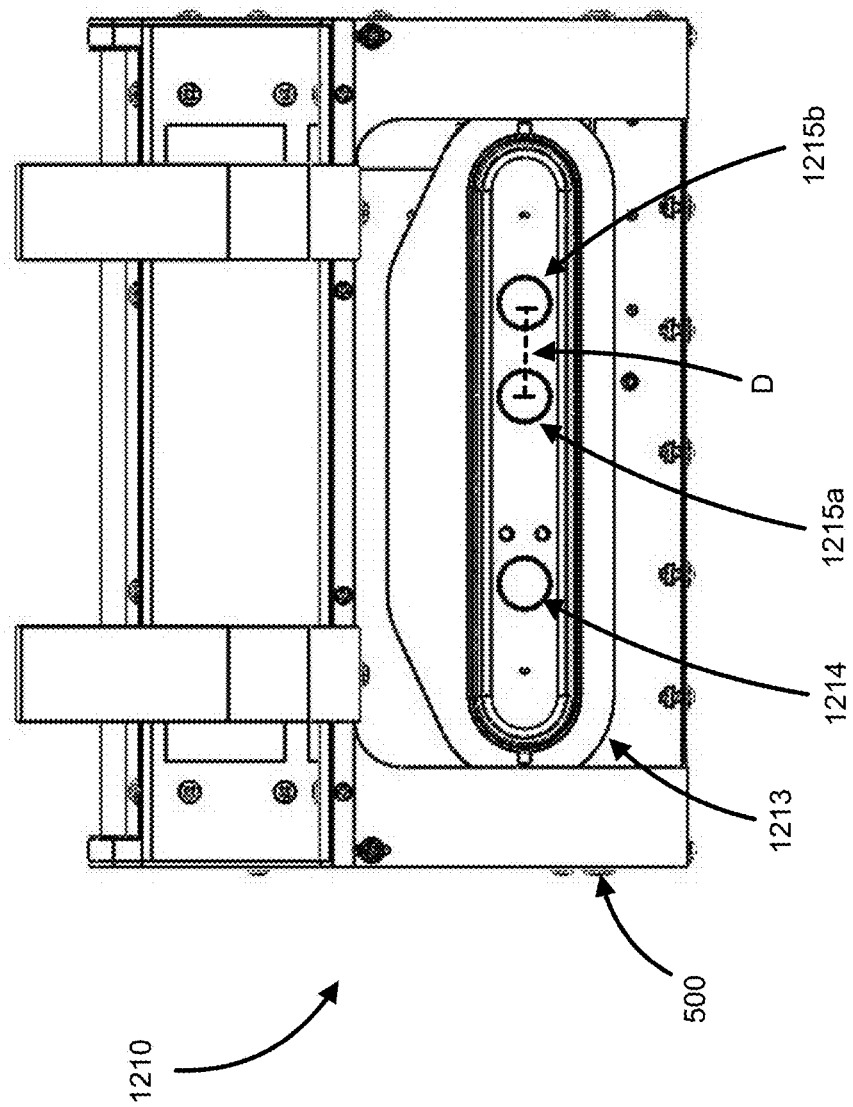
FIG. 5 illustrates a front view of an exemplary exercise monitoring system and camera assembly.

FIG. 5 illustrates a front view of an exercise monitoring assembly 1210 having a camera system 1213, which includes a RGB camera 1214 for viewable optical imaging, and a pair 1215a, 1215b forming a 3D infra-red position/distance encoding camera assembly. The pair of infra-red cameras 1215 are placed a distance D from one another so as to create parallax or stereoscopic viewing of the scene of interest since the precise distance from each of infra-red cameras 1215a and 1215b varies somewhat to a same point in space on account of their geometric offset, which distances can be computed using trigonometric relationships (e.g., in a processor coupled to said infra-red camera sensors 1215a and 1215b). This can be used to create 3D image information that is output from the processor as a data file of pixels, the pixels having respective values being a distance from a reference point (e.g., on exercise monitoring assembly 1210) to an object of interest displayed in the image field (e.g., the user's barbell equipment). In other words, the cameras described above can generate an image file (snapshot or time sequence) that comprises pixels (horizontal and vertical) the values of which are distance values indicating distance from a reference point to an object of interest. As such, the camera system 1213 can be referred to as a 3D imaging system. A processor executing instructions will then be able to compute the time-varying position of the object of interest to generate displacement, velocity, acceleration, force, energy, power, or other result metrics. These computations can be carried out locally on the exercise monitoring assembly 1210 processors and/or remotely on computers coupled to the system 1210 by way of wired or wireless data networks. A data port 500 may be included in the body of the system 1210 to permit plugging the same (e.g., using a USB, serial or other connection) to a communication conduit to exchange data with another local or remote informational apparatus or processor or data storage unit. The system 1210 may be powered by an on-board DC power supply (battery) or may have power cables and/or connections to receive AC or DC power from an outlet feeding the system 1210.

Some aspects of the present invention can benefit from software or machine-readable instructions, operating and executing in conjunction with the described hardware, so as to carry out further features or enable analysis and processing of information. The following paragraphs describe the software components of the technology according to one or more embodiments. It is noted that some embodiments can include additional or fewer software components than the examples described below.

A bar tracking method may rely on the depth image from the 3D camera 1215, in which the value of each pixel corresponds to the distance from that point in space to the aperture of the camera. In a first aspect, this may permit scaling and thresholding of the image to accentuate the bar. In a second aspect, this may allow running convolutional edge detection operations and, e.g., a "Hough transform" to get a 2D equation of a line on the image that corresponds to the pixels in which the bar is located. In a third aspect, this allows determining the distance from the bar to the camera by looking at those pixels in the original depth image. The foregoing steps are merely illustrative and those skilled in the art can appreciate other similar or equivalent or alternative steps to achieve the same objectives or optimize the present system and method for their applications.

To calculate the actual 3D coordinates of the bar in space, it can be useful to know the angle of the camera as it is mounted to the rack. This angle can be determined using data from the accelerometer, which is attached to or included in camera system 1213 and which may be used to generate an output representing camera angle with respect to a reference angle, tile, angular acceleration, etc. Thus, we can determine the angle of the camera, the pixels in the image that represent the bar, and the Euclidean distance from the bar to the camera. With this information, finding the 3D coordinates of the bar is calculated according to the relevant geometry. It should be noted that the RGB color image to more precisely locate the pixels for the bar.

In some embodiments, machine learning, artificial intelligence, or similar concepts are employed to detect, track and deduce useful information from the sensed image data. Machine learning methods, e.g., in the form of neural networks, can be used for fine tuning the parameters of the edge detection operations or to find the spatial coordinates of the bar in an image. Additionally, a properly programmed and trained machine learning model(s) may be used to derive context-sensitive results or to auto-recognize a user (e.g., using face recognition, voice recognition) or any number of other auxiliary automated functions.

Figure 6B:
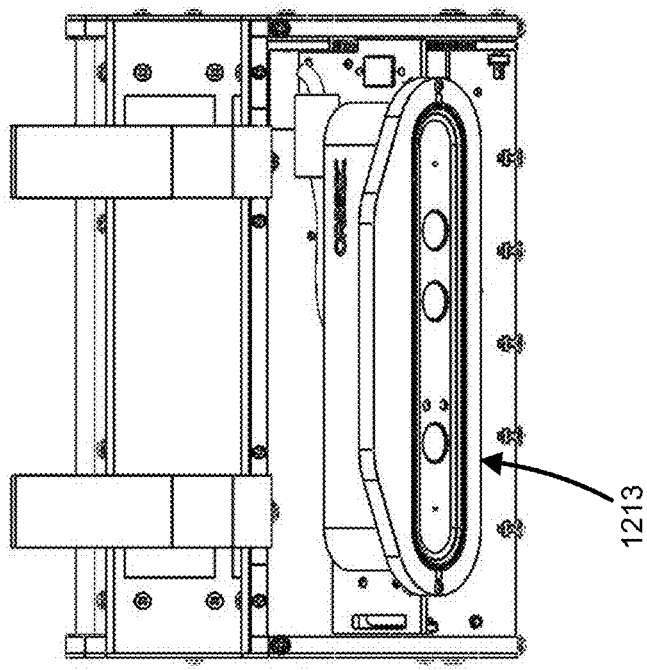
FIGS. 6A and 6B illustrate exemplary front views of an exercise monitoring system with the camera assembly thereof in a tilted (up, down) position.
Figure 6A:
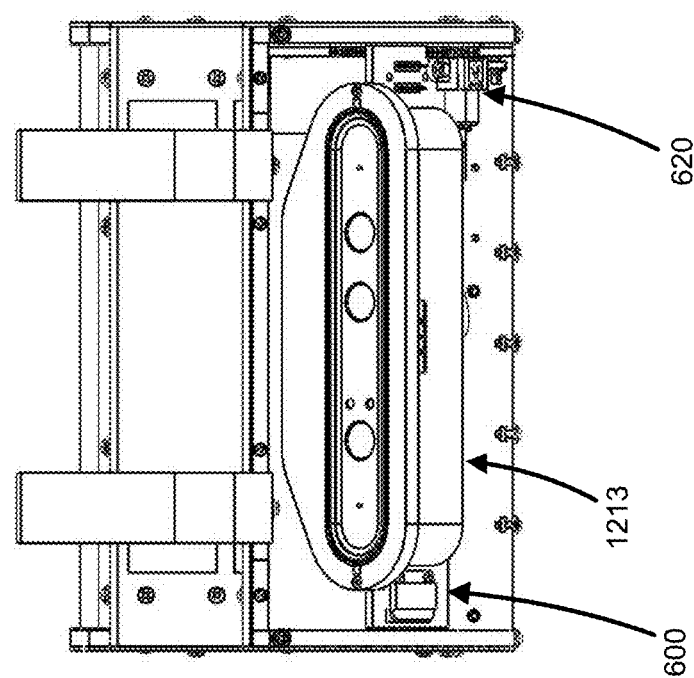

FIGS. 6A and 6B illustrate front views of a exercise monitoring assembly, respectively showing upward-tilted (FIG. 6A) and downward-tilted (FIG. 6B) camera system 1213. The housing of the assembly is not shown so as to illustrate some of the internal components shown. In FIG. 6A an accelerometer 600 or tilt sensor is shown mounted to a pivoting axis or member of the camera system. The accelerometer can also be replaced (or supplemented) with a method that can identify the plane of the floor in the depth image. By mathematically representing the floor, the system is able to calculate the position and orientation of the camera. In FIG. 6B the servo motor or tilt drive 620 is represented, which is used as a prime mover to drive the motorized gears about a pivot axis of camera system 1213 as described in an exemplary embodiment, above.

Figure 7:
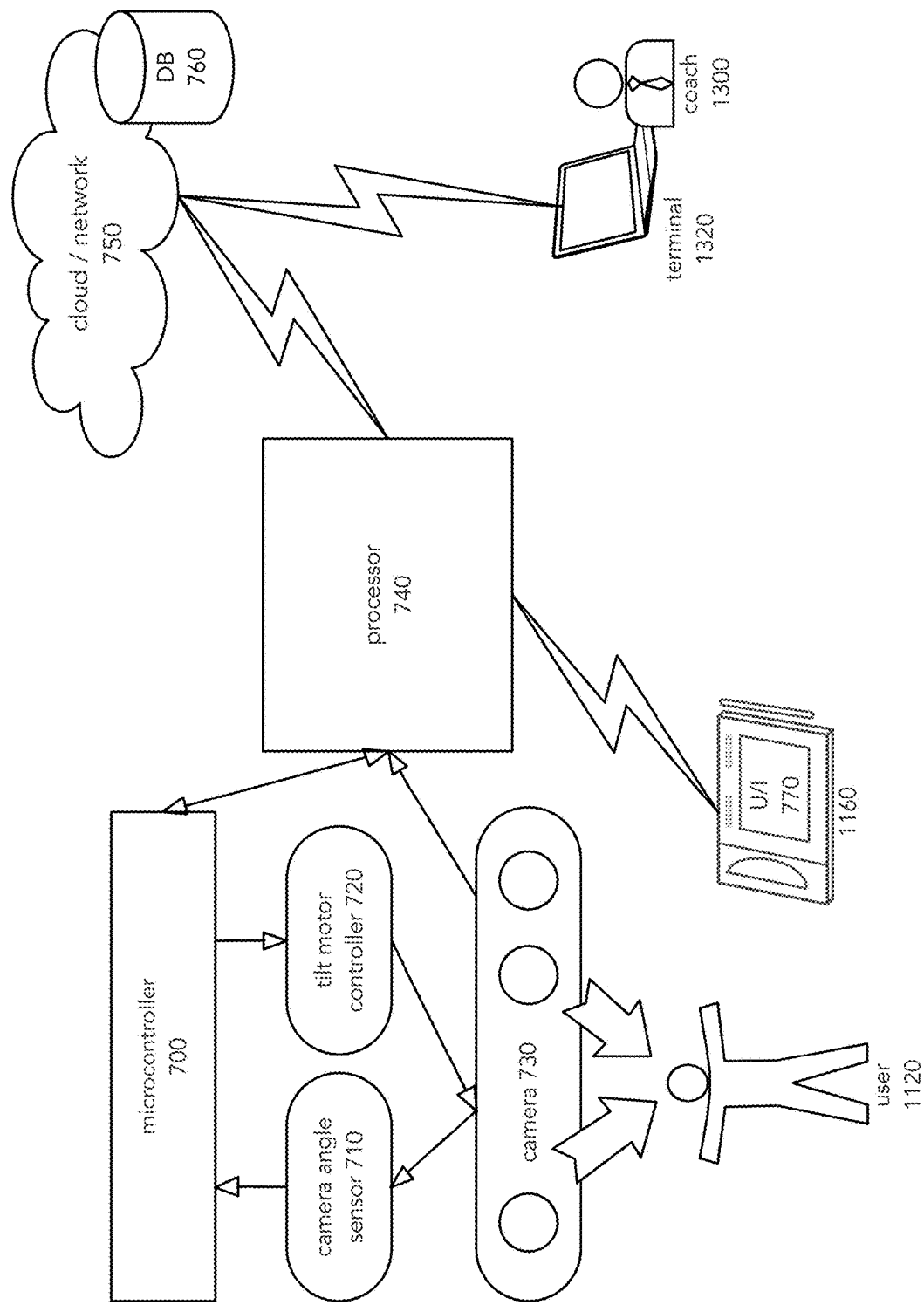
FIG. 7 illustrates a block diagram of some components of a distributed architecture including the present exercise monitoring system and camera assembly.

FIG. 7 is a block diagram that illustrates the hardware and software components of the system. A user 112 is ready to perform a workout (e.g., weight lifting exercise) and presents himself and logs in to the system as described earlier using a user interface (U/I) 770. The U/I 770 may be presented by a mobile or fixed interactive device 1160 such as a tablet device, which is coupled over a communication channel to a processor or computer 740. The system monitors the activity of the user 1120, preferably by optical distance, position, velocity, acceleration and similar measurements on a piece of exercise equipment through a camera system having one or more cameras 730 as disclosed. An angle or tilt sensor (e.g., accelerometer) 710 accounts for movement of the monitored objects in the camera's field of view and tracks the same. A tilt motor (e.g., a servo motor under computer control) 720 drives the movement of the camera 730 as needed. The camera position and movement control is under the control of a microcontroller circuit 700 coupled to said processor 740. Those skilled in the art will appreciate that the illustrated components are exemplary in arrangement, and other arrangements are possible by combining or separating an element into one or more parts.

Processor or local computer 740 is coupled in the present example over a communication network to a cloud or other network 750. Processor 740 may be tasked with image processing, workout processing, or other programmed operations as suitable. Operations that can be performed in the cloud include Web applications, data science infrastructure support, and equipment status monitoring. Stored information can be obtained from or put into a data store (database) 760, which may be coupled to the cloud network 750 or any of the processors or computers of the system. Optionally, a client computer or terminal 1320 can allow a coach, doctor, parent, team mate or other interested party 1300 to monitor the activities of the user 1120. Information passed between processor 740 and interactive device 1160 includes real-time rep velocity, login information and other data.

Figure 8:
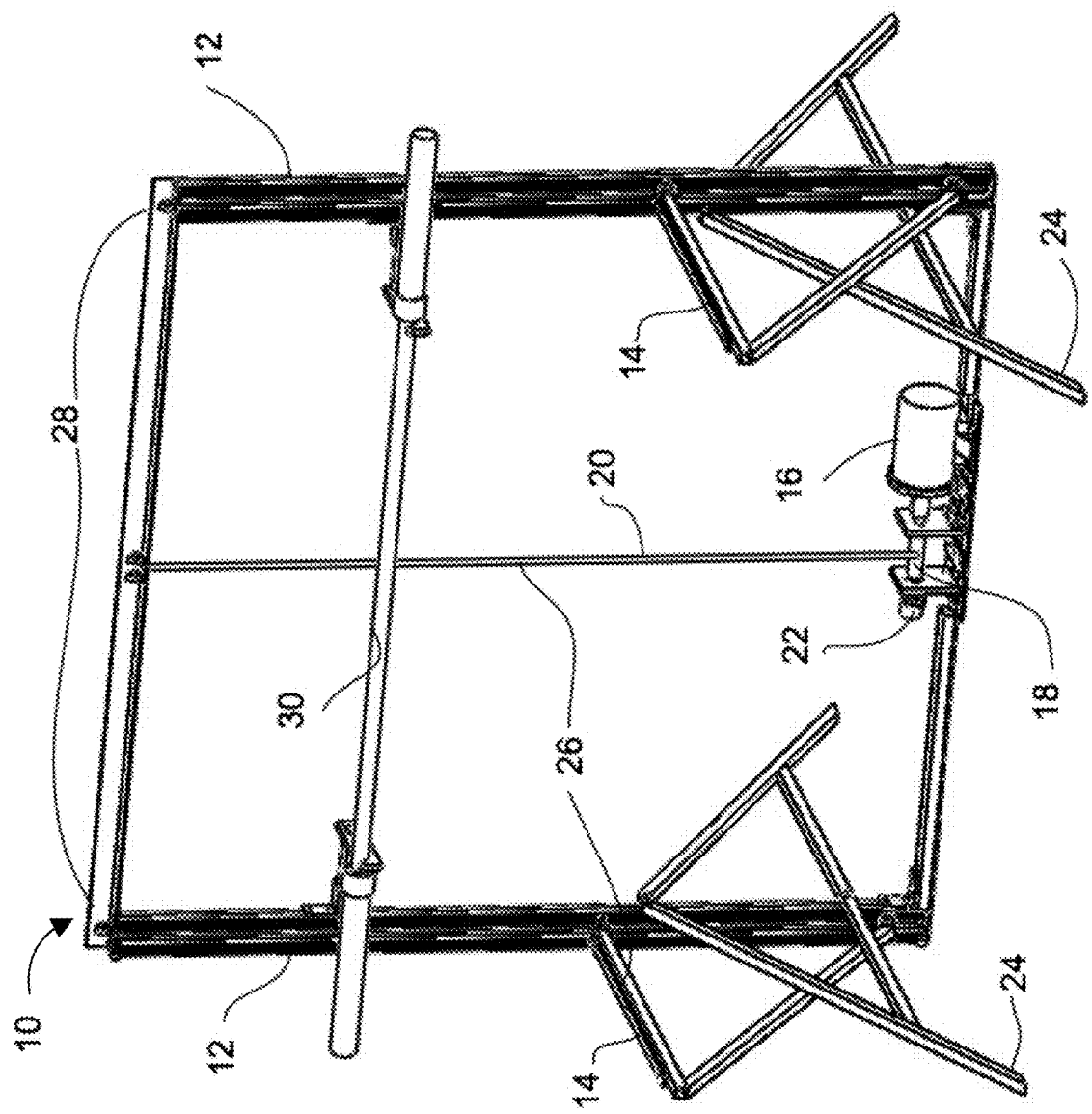
FIG. 8 illustrates an exemplary exercise environment according to aspects of the invention.

FIG. 8 illustrates a barbell rack assembly 10 that can provide automatic spotting or assistance for the weightlifter. The assembly 10 consists of extrusions or bearing slides 12 that are capable of fixing the spotting arms 14 in all degrees of freedom besides up and down. In other words, the bearing slides 12 can allow the arms 14 to move vertically (one degree of freedom) but not horizontally (or any other direction). The arms 14 are actuated by a motor 16. The arms 14 can either be coupled or independently actuated. The motor 16 turns a pulley drum 18 which actuates the arms 14 up and down via a pulley rope 20. The actuation of the arms 14 is not limited to a pulley/winch system. The position of the arms 14 is tracked by an encoder 22 mounted to the pulley drum 18. The encoder 22 can be either a rotary or linear encoder. The rack is supported and kept balanced by two support legs 24. These support legs 24 can be made of welded steel. Load cells 26 in the spotting arms 14 or in line with the pulley rope 20 measure the force output of the motor. A camera vision system 208 mounted to the rack will track the barbell 30 in 3D space.

In some embodiments, the system can track the weightlifter and barbell in 3D space, determine when assistance is needed, and apply a controlled upwards force to the bar when assistance is needed. The force feedback from the load cells can be used to inform the user how much weight the machine is helping to lift. The system can also provide the data and analytics described above.

Figure 9:
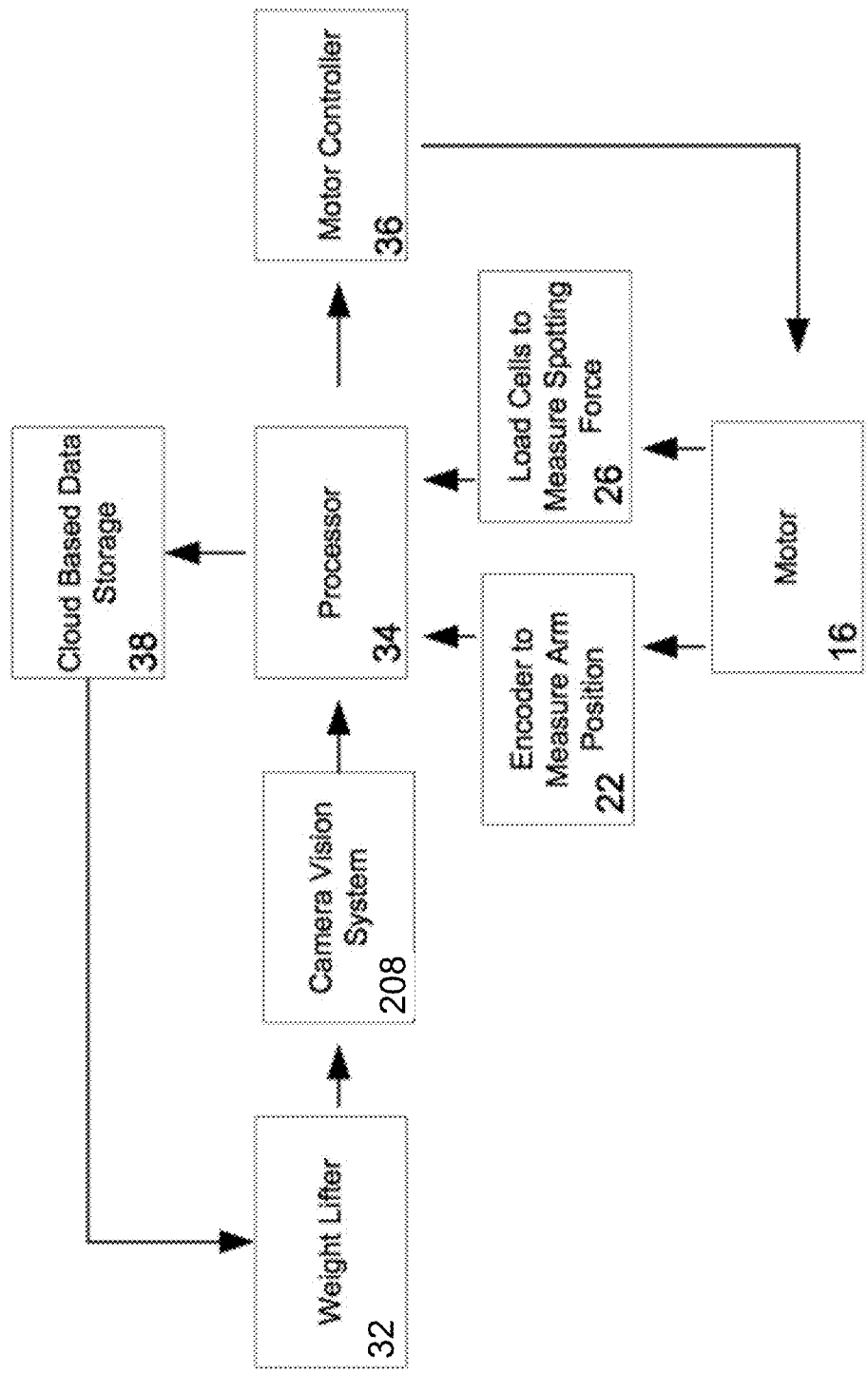
FIG. 9 illustrates another block diagram illustrating the operation of components of the present architecture.

FIG. 9 is an example of a flow diagram of the system illustrated in the previous figure. The weightlifter's 32 position and the position of the barbell 30 will be monitored by the camera vision system 208. This information will be relayed to the processor 34 which will perform the logic in the system and determine what actions to perform. The processor 34 will relay signals to the motor controller 36 which will control the motor 16. The position, velocity, and acceleration of the motor and the force it is applying (to assist/spot the weightlifter 32) will be fed back to the processor via the encoder 22 and the load cells 26. The processor will relay all this information to a cloud based storage system 38 which the weightlifter and trainer 32 will be able to access via their mobile device or computer.

Figure 10:
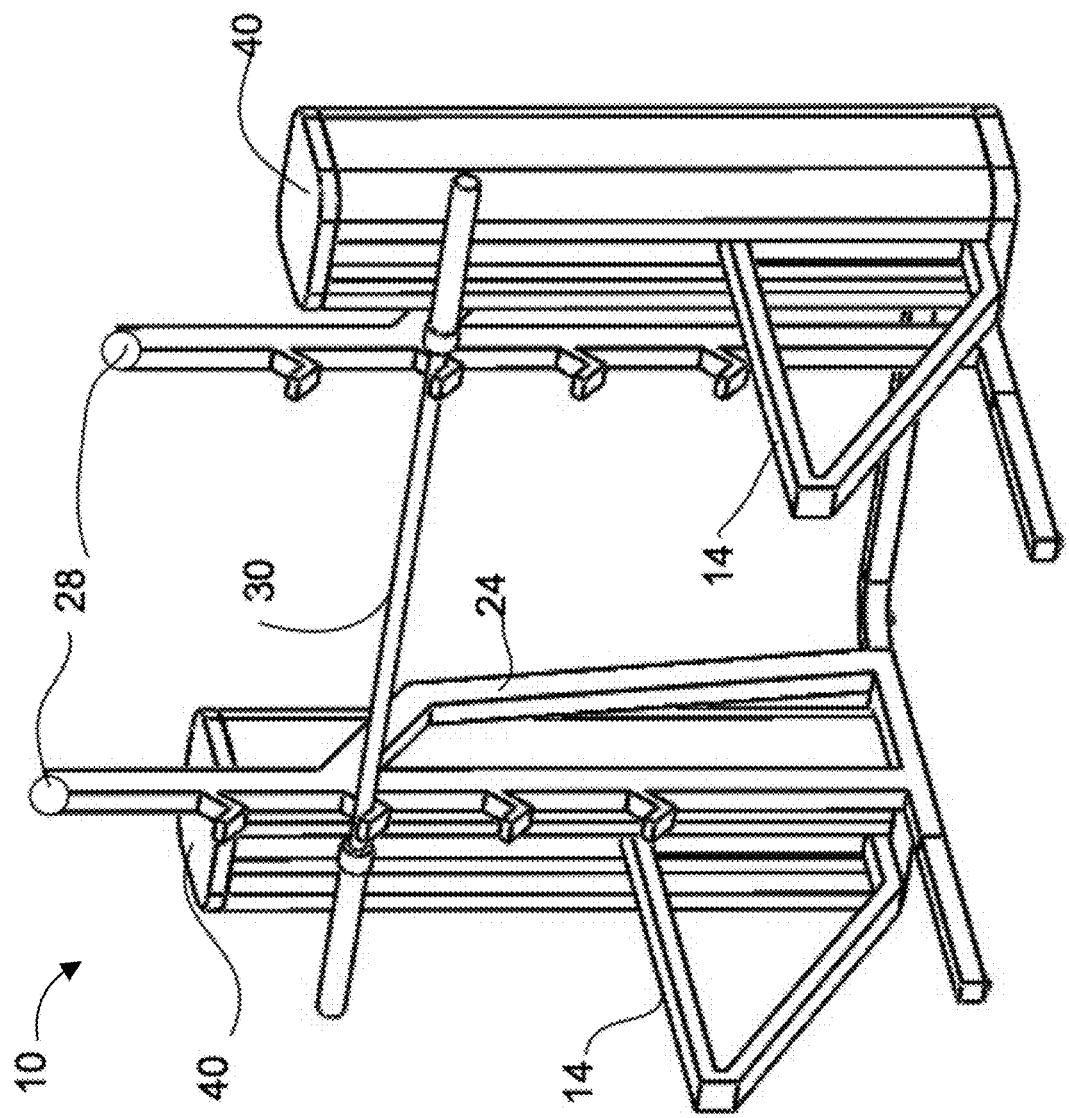
FIGS. 10 through 16 illustrates various aspects and embodiments of an exercise environment consistent with and supported by the present disclosure.

FIG. 10 illustrates another exemplary exercise environment utilizing the present invention. This system comprises a robust, consumer-ready version suitable of being placed in gyms and other facilities. The main frame/assembly 10 consists of the actuated arms 14, the supporting structure 24, and the camera vision system 208. The encoders 22, load cells 26, motor 16 and the electronic components described previously are contained in the housing 40.

Figure 11:
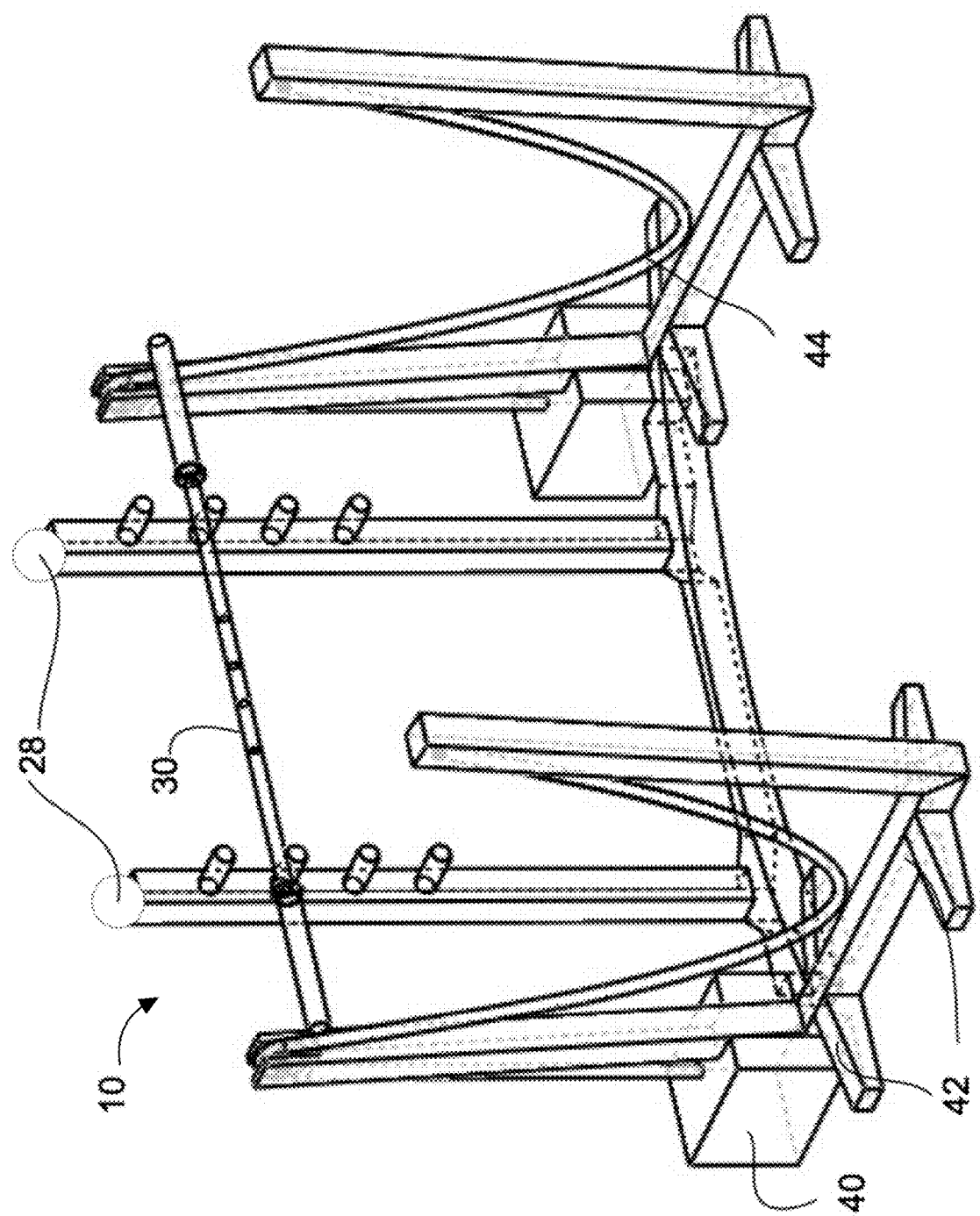

FIG. 11 illustrates yet another embodiment of the automatic spotting system. It shares many similarities to the previously-described embodiments; however, it possesses a different actuation method. It is still a full weight rack and consists of the main frame and assembly 10 which supports the barbell 30. Attached to the main frame and assembly 10 is a belt/rope spotting mechanism 42. This mechanism is similar to the arms 14 as seen before; however, the belt/rope spotting mechanism 42 works by tensioning a belt/rope 44 via a pulley/winch mechanism. The rope/belt will come into contact with the barbell 30 to apply an upwards force. The motor 16 and pulley drum 18 are contained within the housing 40. The camera vision system 208 attached to the main frame/assembly 10 continue to track the barbell 30 and activate the belt/rope spotting mechanism 42 when a spot is needed.

Figure 12:
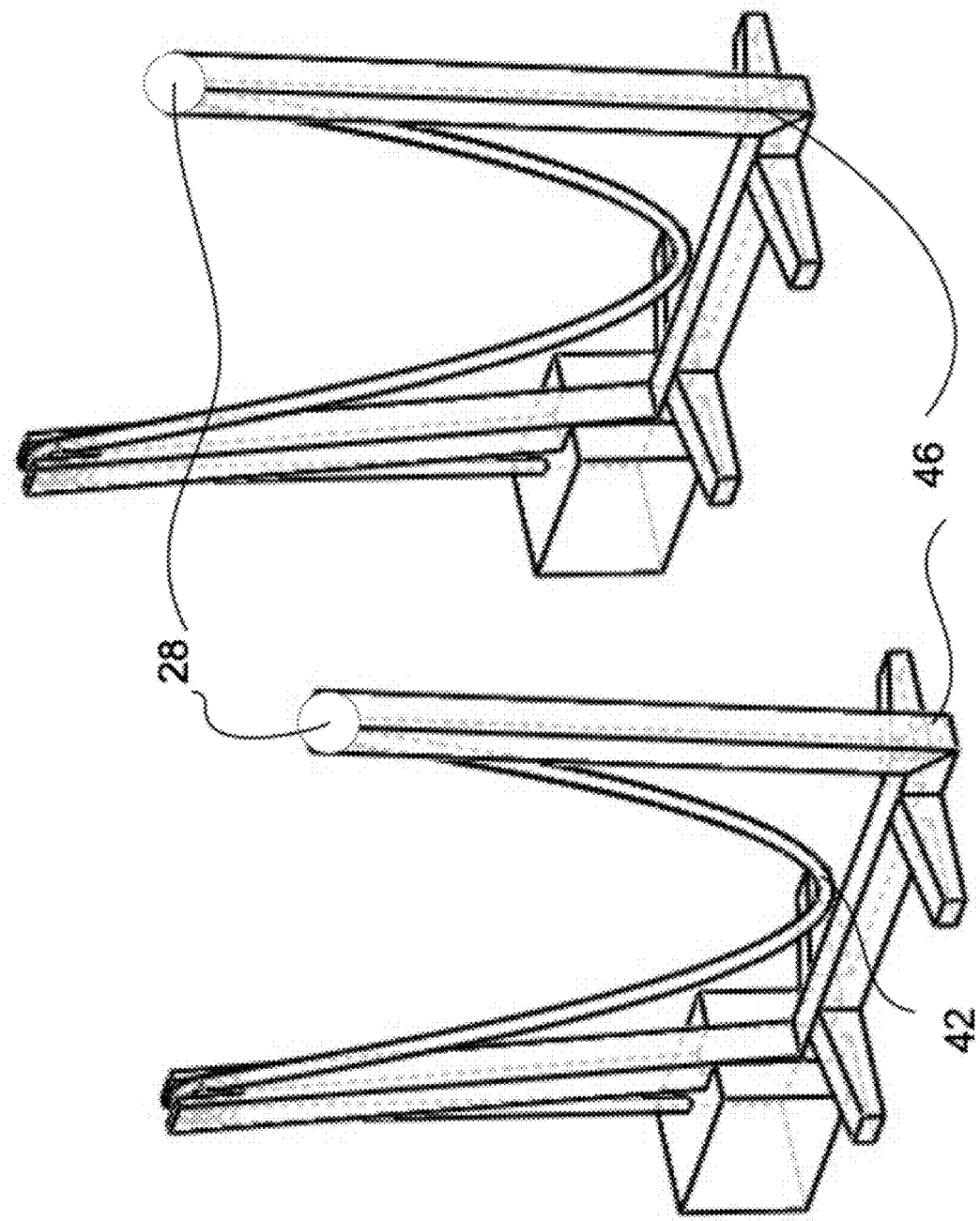

FIG. 12 illustrates a spotting mechanism in the form of an add-on system. The two moveable spotting mechanisms 46 will be light and easy to move around, allowing the weightlifter to position them next to any pre-existing rack and in any position they want. This embodiment uses the rope/belt spotting mechanism 42; however, it is not limited to this mechanism. It can use rigid arms 14 that can be linearly actuated in a number of different ways, for example as described above. The two moveable spotting mechanisms 46 will contain the camera vision system 208.

Figure 13:
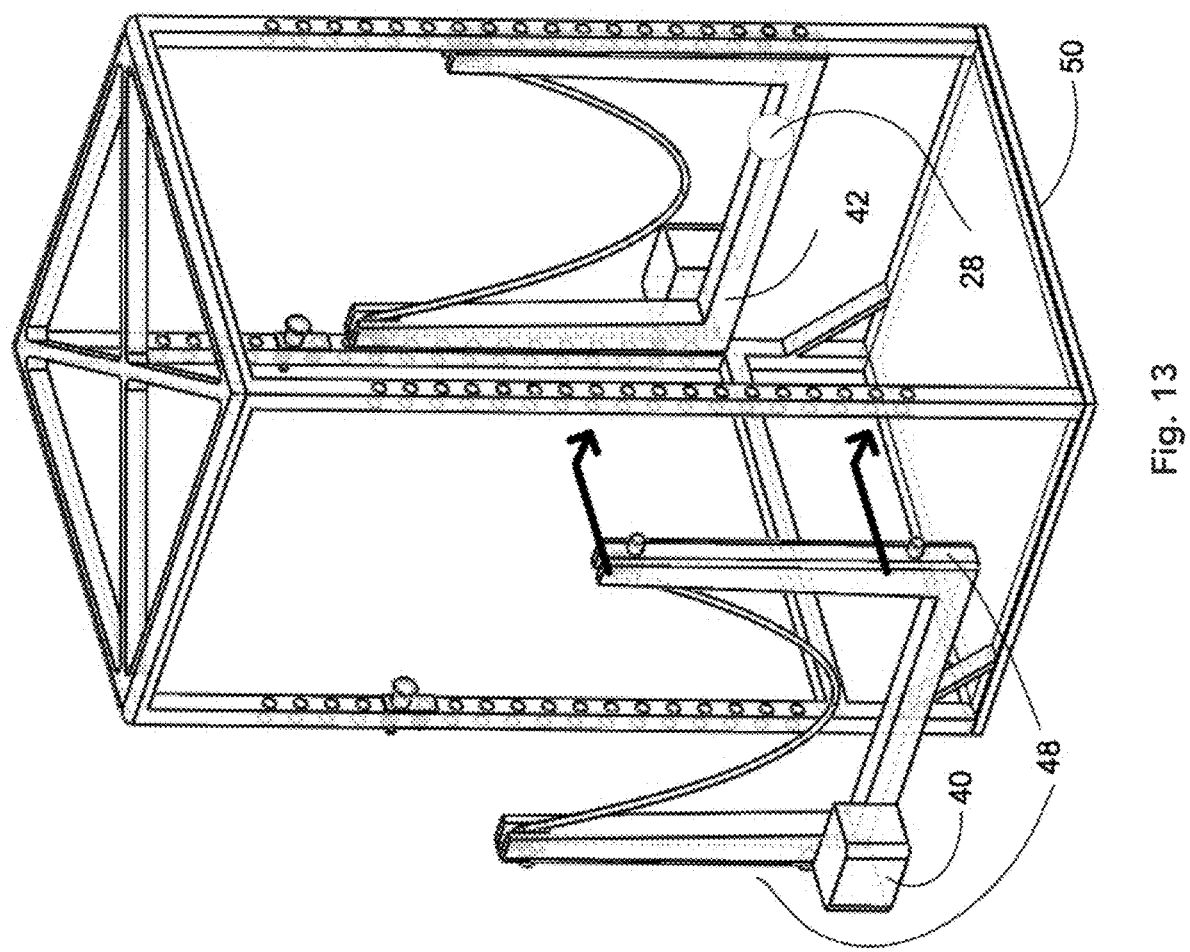

FIG. 13 illustrates another embodiment of the spotting mechanism. This embodiment is also an add-on system, but it is not stand alone. It has a mounting mechanism 48 which will allow it to be attached to any pre-existing bench or squat rack 50. The rack using a belt/rope spotting mechanism 42 but it is not limited to this spotting mechanism. It can use rigid arms 14 actuated by a variety of linear actuation methods. This add-on system will contain the camera vision system 208 and still be able to spot and track the user.

At least some of the embodiments are formed of steel and aluminum extrusions which have been either welded or screwed together. However, this is not limiting as those skilled in the art may understand that present or future technologies can be employed to accomplish substantially the same result using other materials, e.g., carbon fiber, polymer materials or others.

Some or all embodiments of the present method and system allow for ease of installation. Using smart hardware and software, coaches (or anyone else) can install the camera by themselves onto any rack. The camera can be easily calibrated and does not require professional installation. For example, the system (hardware, software, other features) may be shipped to coaches and they can take care of the rest of the setup and installation thereof. This is an improvement over existing systems that require the customer to partner with weight rack manufacturers and require professional installation.

The present system and method can also improve bar tracking, providing more reliable results.

Additionally, the present system and methods are less intrusive from the perspective of users and coaches. By utilizing machine learning it can be possible to incorporate facial recognition, voice recognition, exercise recognition, and more, in order to make the product as easy to use as possible.

The present system and method are also relatively cost effective. Smart hardware design can be used to minimize system costs. For example, the product can be made easy to install and does not require professional installation.

The present system and method are convenient for collecting data and using data try to learn more about the human body, e.g., data analytics.

Additionally, the present system and method can provide for joint tracking to recognize body position in 3D space. This can provide athletes and coaches with more insight into their form and workout and it will not limit the tracking to barbell exercises.

The use of a camera in some or all embodiments allows the system to operate without, or with minimal, contact to the lifting mechanisms/bars so as to avoid change to or impact on the workout experience. However, the use of an optical camera is not required in all embodiments of the present system and method, for example if a camera-enabled system or associated image processors is too expensive or not suited for a certain application.

Figure 14:
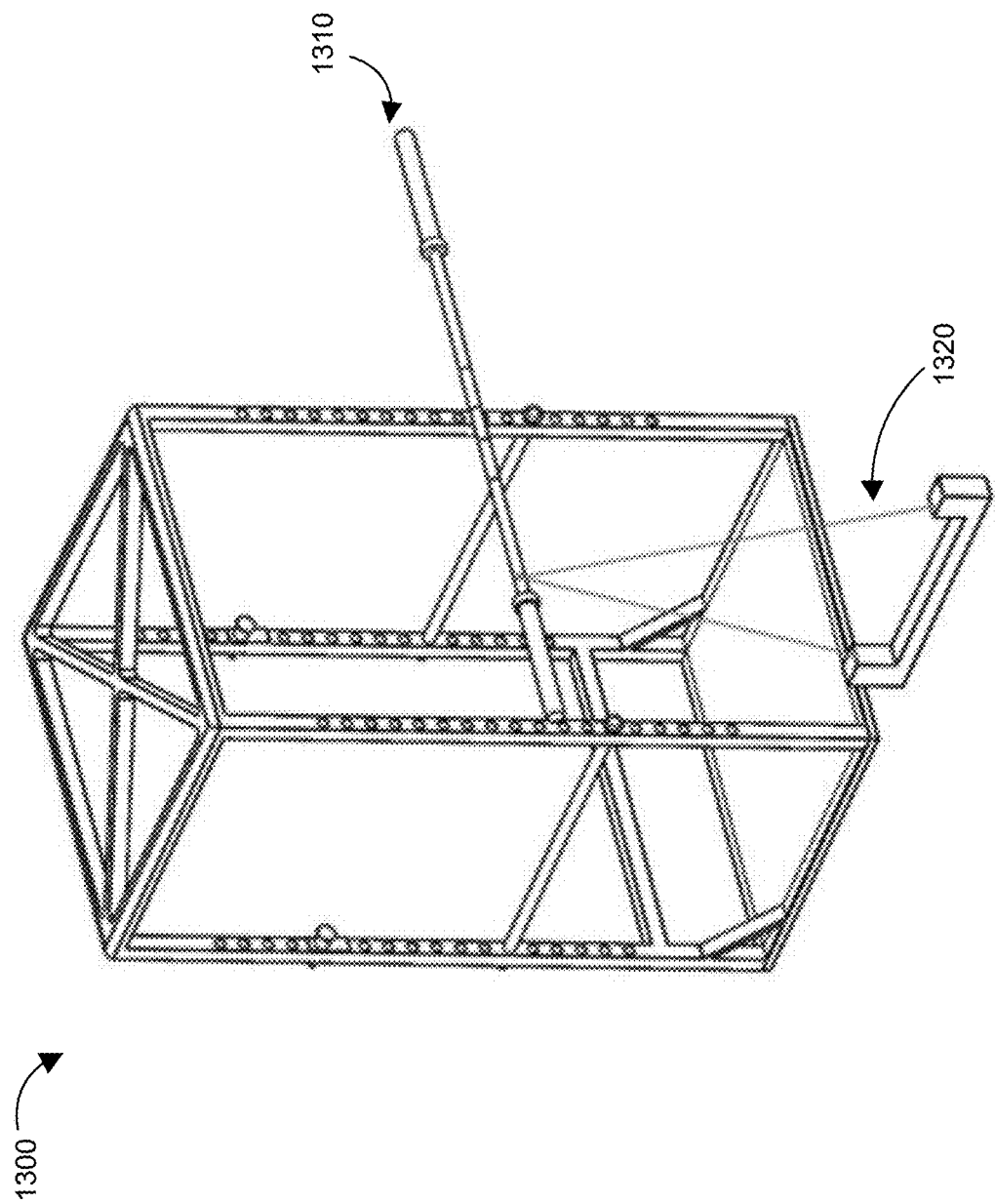

FIG. 14 illustrates another embodiment of the present system 1300 where a mechanical structure incorporating an exercise apparatus and one or moving parts, e.g. a weight bar 1310. A string, wire, cord or similar fixed-length extendable tether 1320 is placed on or around bar 1310 and will extend therewith as bar 1310 is moved. The movement of bar 1310 will accordingly be sensed by strings 1320, including the displacement, velocity, and acceleration of bar 1310. The measurement can be made so in one or more directions by using corresponding string systems 1320. Information from the movement of the string-bar assembly can be transmitted and recorded and used as described earlier with regard to photographic sensing of bar movement. In one embodiment, a rotational encoder is used to generate quantitative output signals corresponding to the motion of string 1320. The rotational encoder may be coupled to a constant force spring, which provides a minimal resistance force but ensures that the strings 1320 are under sufficient tension to retract and remain straight and taught. In other embodiments, a small motor connected to a closed-loop feedback controller can apply a small torque to strings 1320.

Figure 15:
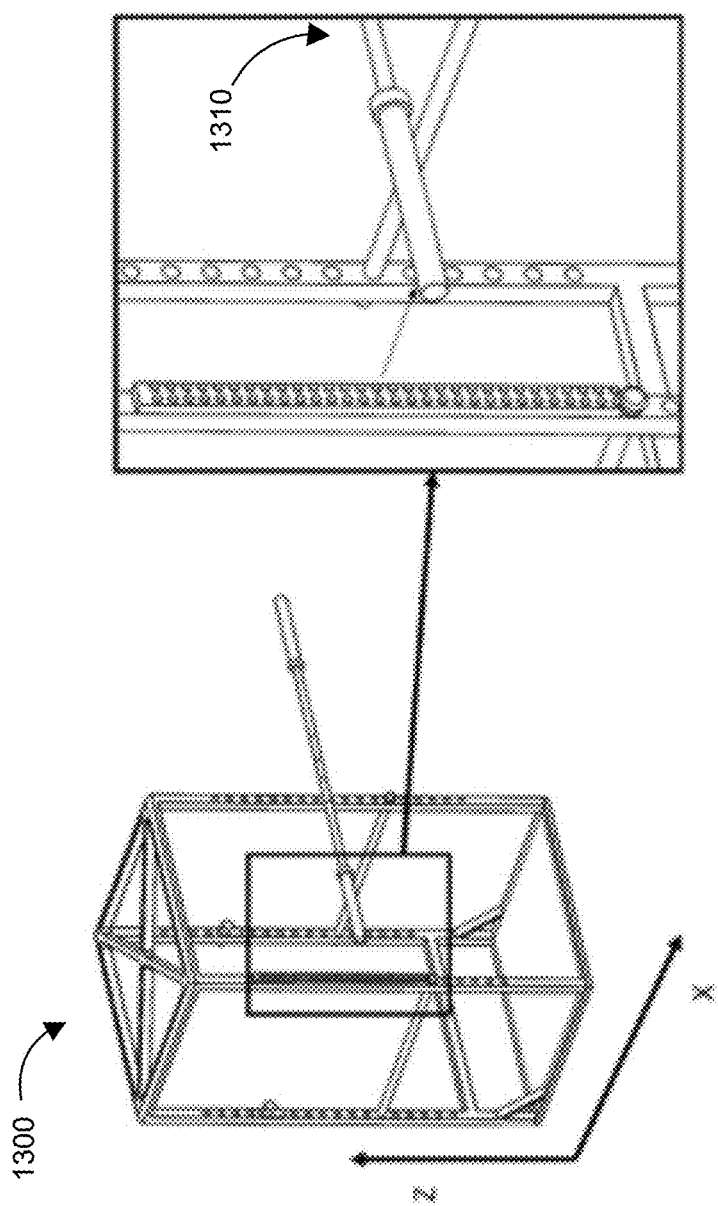

As mentioned above, more than one degree of freedom or dimension can be monitored as stated, including by using a second or third or more rotational encoders, motors, strings, etc. For example, having two sets of strings and encoders would allow for two-dimensional operation in, e.g., the x-y or x-z plane. FIG. 15 shows the two-dimensional nature and degrees of freedom possible in one example.

Figure 16:
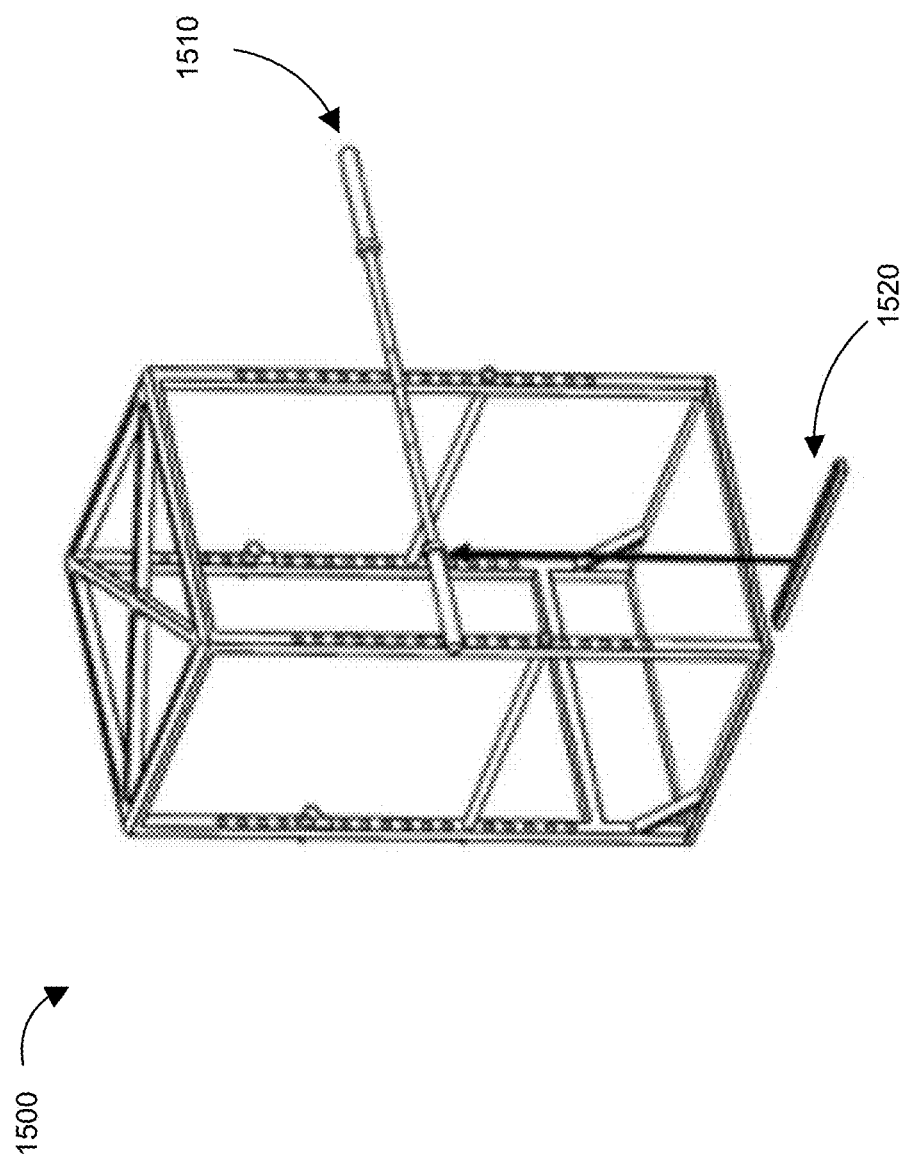

FIG. 16 illustrates yet another embodiment of an exercise system 1500 including at least one moveable mechanical member (e.g., a weight bar) 1510 that moves in at least one direction during use (e.g., up and down). The position of the bar 1510 can be monitored by one or more ultrasonic sensors 1520, including in an example, by an array of ultrasonic sensors. The sensors 1520 can be disposed below the bar 1510 and direct an ultrasound beam upwardly towards the bar 1510. Pulse-echo, sonar or similar transmission and reflection of energy from the moving bar 1510 is used to determine a distance from the sensor 1520 to the bar 1510 (or, equivalently to any suitable reference position). The position of bar 1510 can be measured repeatedly at some intervals (e.g., regular intervals) and used to compute a velocity of the bar or an acceleration or other measurements. This embodiment is not limited to ultrasound but can be extended to other means such as optical light, laser, or any suitable instrumentality.

Yet other aspects allow for automatic spotting. While spotting is not a necessary or required feature of all present embodiments, in the case the system is used for spotting, the present system and method improves a weightlifter's safety and makes weightlifting more accessible. Also, it provides the user with information about how much weight was removed by the spot.

It is to be appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. Variations and modifications of the embodiments described herein, which would occur to persons skilled in the art upon reading the foregoing description, are contemplated by and included in this disclosure.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein. The present materials, methods, and examples are illustrative only and not intended to be limiting.

We claim:

1. An exercise monitoring system for use with exercise equipment, comprising:
    a camera assembly comprising:
        a first camera that captures first visible light images of a user of said exercise equipment, and
        a second camera that generates an image comprising a matrix of distance values;
    a motorized driver, mechanically coupled to said camera assembly within a housing, that moves said camera assembly in at least one degree of freedom to track a movement of at least one object in a field of view of said at least one imaging sensor;
    a processor coupled to said camera assembly and receiving said matrix of distance values from said camera assembly, said processor further performing analysis of said matrix of distance values to generate information relating to monitored exercise activity of said user;
    a controller, in data communication with said processor, and coupled to said motorized driver, which controls movement of said motorized driver so as to track the movement of said object;
    said housing containing each of said camera assembly, motorized driver, processor and controller, the housing mechanically coupled to said motorized driver to move the camera assembly with respect to said housing, and further configured to mechanically couple said exercise monitoring system to an external support;
    the system further comprising:
    an interactive device, physically separate from said housing, said interactive device configured to receive and display said information relating to monitored exercise activity of said user, wherein said interactive device further comprises a front-facing camera that captures second visible light images of said user, said second visible light images taken from a different perspective than said first visible light images, and
    wherein said first visible light images, said second visible light images, and said information relating to monitored exercise activity of said user are transmitted to a remote database for storage.

2. The system of claim 1, said first camera comprising a visible light image capture camera assembly.

3. The system of claim 1, said second camera comprising a three-dimensional camera assembly.

4. The system of claim 3, said three-dimensional camera assembly comprising a plurality of infra-red image sensors, spatially separated from one another and configured and arranged to capture respective infra-red imagery and further being coupled to a processor that computes a position for each pixel in a multi-pixel position image based on said infra-red imagery from each of the plurality of infra-red image sensors.

5. The system of claim 3, said three-dimensional camera assembly comprising a plurality of visible light image sensors, spatially separated from one another and configured and arranged to capture respective visible light imagery and further being coupled to a processor that computes a position for each pixel in a multi-pixel position image based on said visible light imagery from each of the plurality of visible light image sensors.

6. The system of claim 1, said housing further comprising one or more mechanical attachment members that secure the system to a support member of said exercise equipment.

7. The system of claim 6, said mechanical attachment members comprising a strap that secures the system to a support member of said exercise equipment or another fixed member with respect thereto.

8. The system of claim 1, said motorized driver comprising a motor that applies reversible torque through a gear to rotate said camera assembly about an axis of rotation to adjust an angular position of said camera assembly with respect to said housing.

9. The system of claim 1, further comprising a communications module.

10. The system of claim 1, further comprising a tilt angle sensor that determines an angular position or displacement of said camera assembly and provides an output indicative of said angular position or displacement.

11. The system of claim 10, said tilt angle sensor comprising an accelerometer.

12. The system of claim 1, wherein said interactive device is in data communication with said system's processor, and including an interactive device processor in the interactive device, a user interface display, and instructions stored and executed in said interactive device processor and including instructions implementing an exercise activity program on said interactive device.

13. The system of claim 1, further comprising a server, in data communication with said system's processor, the server including a server processor executing instructions therein implementing a machine learning program running on the processor and trained on said server.

14. The system of claim 1, said processor and said controller being integrated into a common circuit on a circuit board disposed in said housing.

15. A method for tracking an exercise routine of a user, comprising:
    providing an exercise monitoring system in a housing mountable to an exercise machine;
    collecting first visible light images using a first camera in said housing;
    collecting imagery using at least one distance-measuring camera assembly in said exercise monitoring system, the imagery containing information regarding an object of interest in said exercise machine;
    generating a multi-pixel position image from said imagery that codifies, for each pixel in the multi-pixel position image, a distance from a reference point to a corresponding point on said object of interest;
    performing analysis of said multi-pixel position image to generate information relating to monitored exercise activity of said user; and
    moving said camera assembly of said exercise monitoring system with respect to the housing, using a motorized driver within and mechanically coupled to said housing, as necessary to track a position of said object of interest and to keep said object of interest within a field of view of said camera apparatus,
    wherein providing said exercise monitoring system includes disposing said distance-measuring camera assembly and a motor and a motor controller configured and arranged to controllably move said camera assembly within said housing;

receiving and displaying, via an interactive device that is physically separate from said housing, said information relating to monitored exercise activity of said user, capturing, using a front-facing camera of said interactive device, second visible light images of said user, said second visible light images taken from a different perspective than said first visible light images, and transmitting to a remote database for storage said first visible light images, said second visible light images, and said information relating to monitored exercise activity of said user.

16. The method of claim 15, further comprising presenting to a user of said exercise monitoring system, on said interactive device, information regarding the user's performance on said exercise machine.

17. The method of claim 15, further comprising accepting from a user of said exercise monitoring system, via an interactive device coupled thereto, user identification information to log the user in to an interactive program running on said interactive device.

18. The method of claim 15, further comprising exchanging real-time data between said interactive device and a server coupled to said interactive device over a data communication network.

19. The method of claim 15, further comprising calculating one or more metrics regarding a performance of said user on said exercise machine.

20. The method of claim 15, further comprising implementing a biometric recognition step on said interactive device so as to recognize a user.

21. The method of claim 20, said biometric recognition step including a step of facial recognition of said user.

* * * * *